(12) United States Patent
Krueger

(10) Patent No.: US 12,133,567 B2
(45) Date of Patent: Nov. 5, 2024

(54) SYSTEMS AND METHODS FOR USING EYE IMAGING ON FACE PROTECTION EQUIPMENT TO ASSESS HUMAN HEALTH

(71) Applicant: Wesley W. O. Krueger, San Antonio, TX (US)

(72) Inventor: Wesley W. O. Krueger, San Antonio, TX (US)

(*) Notice: Subject to any disclaimer, the term of this patent is extended or adjusted under 35 U.S.C. 154(b) by 0 days.

(21) Appl. No.: 18/406,199

(22) Filed: Jan. 7, 2024

(65) Prior Publication Data

US 2024/0156189 A1 May 16, 2024

Related U.S. Application Data

(63) Continuation-in-part of application No. 17/989,429, filed on Nov. 17, 2022, now abandoned, which is a continuation-in-part of application No. 17/576,673, filed on Jan. 14, 2022, now Pat. No. 11,504,051, which is a continuation-in-part of application No. 16/903,136, filed on Jun. 16, 2020, now Pat. No.

(Continued)

(51) Int. Cl.
| | |
|---|---|
| *A41D 13/11* | (2006.01) |
| *A61B 3/14* | (2006.01) |
| *A61B 5/00* | (2006.01) |
| *A61B 5/16* | (2006.01) |
| *G16H 10/60* | (2018.01) |
| *G16H 20/00* | (2018.01) |
| *G16H 50/20* | (2018.01) |

(52) U.S. Cl.
CPC ............ *A41D 13/1184* (2013.01); *A61B 3/14* (2013.01); *A61B 5/165* (2013.01); *A61B 5/4064* (2013.01); *A61B 5/4088* (2013.01); *A61B 5/4848* (2013.01); *A61B 5/742* (2013.01); *G16H 10/60* (2018.01); *G16H 20/00* (2018.01); *G16H 50/20* (2018.01)

(58) Field of Classification Search
CPC ....... A41D 13/1184; A61B 3/14; A61B 5/165; A61B 5/4064; A61B 5/4088; A61B 5/4848; A61B 5/742; G16H 10/60; G16H 20/00; G16H 50/20
USPC ......................................................... 600/300
See application file for complete search history.

(56) References Cited

U.S. PATENT DOCUMENTS

| | | | |
|---|---|---|---|
| 3,616,463 | A | 11/1971 | Theodore et al. |
| 4,817,633 | A | 4/1989 | McStravick et al. |

(Continued)

FOREIGN PATENT DOCUMENTS

WO    2013117727    8/2013

OTHER PUBLICATIONS

Allison et al. Combined Head and Eye Tracking System for Dynamic Testing of the Vestibular System. IEEE Transactions on Biomedical Engineering. vol. 43 No. 11, Nov. 1996 (USA).

*Primary Examiner* — Mohammed A Hasan

(57) ABSTRACT

Face protection equipment that comprises an eye imaging module for measuring an eye component (such as a retina, sclera, cornea, iris, limbus, pupil, or eyelid), can be used to measure an ocular parameter (such as saccades, vergence, smooth pursuit, gaze, eye fixation, pupil size, or eyeblinks). This ocular parameter measurement can then be used to assess human health, such as a traumatic brain injury. It can also be used to develop and implement ocular training protocols on a user-viewable display, and to assess the effects of a pharmacologic intervention.

20 Claims, 11 Drawing Sheets

Related U.S. Application Data 11,490,809, which is a continuation-in-part of application No. 16/264,242, filed on Jan. 31, 2019, now Pat. No. 10,716,469, which is a continuation-in-part of application No. 15/713,418, filed on Sep. 22, 2017, now Pat. No. 10,231,614, which is a continuation-in-part of application No. 15/162,300, filed on May 23, 2016, now Pat. No. 9,788,714, which is a continuation-in-part of application No. 14/326,335, filed on Jul. 8, 2014, now Pat. No. 9,370,302, said application No. 16/264,242 is a continuation-in-part of application No. 13/749,873, filed on Jan. 25, 2013, now abandoned, said application No. 17/576,673 is a continuation-in-part of application No. 16/805,253, filed on Feb. 28, 2020, now Pat. No. 11,389,059.

(56) References Cited

U.S. PATENT DOCUMENTS

| | | |
|---|---|---|
| 5,180,907 A | 1/1993 | Udden et al. |
| 5,204,998 A | 4/1993 | Liu |
| 5,550,601 A | 8/1996 | Donaldson |
| 5,555,895 A | 9/1996 | Ulmer et al. |
| 5,621,922 A | 4/1997 | Russ |
| 5,838,420 A | 11/1998 | Donaldson et al. |
| 5,919,149 A | 7/1999 | Allum |
| 5,942,954 A | 8/1999 | Galiana et al. |
| 5,953,102 A | 9/1999 | Berry |
| 5,978,972 A | 11/1999 | Steward et al. |
| 6,301,718 B1 | 10/2001 | Rigal |
| 6,796,947 B2 | 9/2004 | Watt et al. |
| 6,826,509 B2 | 11/2004 | Crisco et al. |
| 6,931,671 B2 | 8/2005 | Skiba |
| 7,276,458 B2 | 10/2007 | Wen |
| 7,380,938 B2 | 6/2008 | Chmielewski et al. |
| 7,386,401 B2 | 6/2008 | Vock et al. |
| 7,401,920 B1 | 7/2008 | Kranz et al. |
| 7,448,751 B2 | 11/2008 | Kiderman et al. |
| 7,500,752 B2 | 3/2009 | Nashner |
| 7,509,835 B2 | 3/2009 | Beck |
| 7,526,389 B2 | 4/2009 | Greenwald et al. |
| 7,651,224 B2 | 1/2010 | Wood et al. |
| 7,682,024 B2 | 3/2010 | Plant et al. |
| 7,727,162 B2 | 6/2010 | Peterka |
| 7,731,360 B2 | 6/2010 | MacDougall et al. |
| 7,753,523 B2 | 7/2010 | Kiderman et al. |
| 7,849,524 B1 | 12/2010 | Williamson et al. |
| 7,866,818 B2 | 1/2011 | Schroeder et al. |
| 7,931,370 B2 | 4/2011 | Bartomeu |
| 7,988,287 B1 | 8/2011 | Butler et al. |
| 8,232,881 B2 | 7/2012 | Hertz |
| 8,253,814 B2 | 8/2012 | Zhang et al. |
| 8,285,416 B2 | 10/2012 | Cho et al. |
| 8,510,166 B2 | 8/2013 | Neven |
| 8,529,463 B2 | 9/2013 | Della Santina et al. |
| 8,578,520 B2 | 11/2013 | Halldin |
| 8,696,126 B2 | 4/2014 | Yoo et al. |
| 8,764,193 B2 | 7/2014 | Kiderman et al. |
| 10,191,294 B2 | 1/2019 | Macnamara |
| 10,535,151 B2 | 1/2020 | Bleyer et al. |
| 2002/0118339 A1 | 8/2002 | Lowe |
| 2002/0176051 A1* | 11/2002 | Saladin ............... A61B 3/032 351/239 |
| 2006/0059606 A1 | 3/2006 | Ferrara |
| 2006/0098087 A1 | 5/2006 | Brandt et al. |
| 2006/0270945 A1 | 11/2006 | Ghajar |
| 2008/0022441 A1 | 1/2008 | Oranchak et al. |
| 2009/0021695 A1 | 1/2009 | Scarpino |
| 2010/0036289 A1 | 2/2010 | White et al. |
| 2010/0092049 A1 | 4/2010 | Schroeder et al. |
| 2010/0101005 A1 | 4/2010 | Cripton et al. |
| 2010/0198104 A1 | 8/2010 | Schubert et al. |
| 2010/0280372 A1 | 11/2010 | Poolman et al. |
| 2011/0176106 A1 | 7/2011 | Lewkowski |
| 2011/0209272 A1 | 9/2011 | Drake |
| 2012/0133892 A1 | 5/2012 | Furman et al. |
| 2012/0143526 A1 | 6/2012 | Benzel et al. |
| 2012/0194551 A1* | 8/2012 | Osterhout ............ G06F 3/005 345/633 |
| 2012/0198604 A1 | 8/2012 | Weber et al. |
| 2012/0204327 A1 | 8/2012 | Faden et al. |
| 2012/0297526 A1 | 11/2012 | Leon |
| 2013/0232668 A1 | 9/2013 | Suddaby |
| 2013/0278899 A1 | 10/2013 | Waldorf et al. |
| 2014/0111771 A1 | 4/2014 | Liu |
| 2014/0171756 A1 | 6/2014 | Waldorf et al. |
| 2014/0192326 A1 | 7/2014 | Kiderman et al. |
| 2014/0327880 A1 | 11/2014 | Kiderman et al. |
| 2015/0038803 A1 | 2/2015 | Uhlig et al. |
| 2015/0051508 A1 | 2/2015 | Ghajar et al. |
| 2015/0223683 A1 | 8/2015 | Davidovics et al. |
| 2015/0243099 A1 | 8/2015 | Schowengerdt |
| 2015/0245766 A1 | 9/2015 | Rennaker et al. |
| 2015/0335239 A1 | 11/2015 | MacDougall |
| 2016/0033750 A1 | 2/2016 | Nunnink et al. |
| 2016/0062459 A1 | 3/2016 | Publicover et al. |
| 2016/0081546 A1 | 3/2016 | MacDougall |
| 2016/0085302 A1 | 3/2016 | Publicover et al. |
| 2016/0106315 A1 | 4/2016 | Kempinski |
| 2016/0110920 A1 | 4/2016 | Schowengerdt |
| 2016/0132726 A1 | 5/2016 | Kempinski et al. |
| 2016/0262608 A1* | 9/2016 | Krueger ............... G16H 40/63 |

\* cited by examiner

SYSTEMS AND METHODS FOR USING EYE IMAGING ON FACE PROTECTION EQUIPMENT TO ASSESS HUMAN HEALTH

CROSS REFERENCE TO RELATED APPLICATIONS

This application is a continuation-in-part of U.S. patent application Ser. No. 17/989,429, which is a continuation-in-part of U.S. patent application Ser. No. 17/576,673, filed 14 Jan. 2022, now U.S. Pat. No. 11,504,051, which is a continuation-in-part of U.S. patent application Ser. No. 16/903,136 filed 16 Jun. 2020, now U.S. Pat. No. 11,490,809, which is a continuation in part of U.S. patent application Ser. No. 16/264,242 filed 31 Jan. 2019, now U.S. Pat. No. 10,716,469, which is a continuation-in-part of U.S. patent application Ser. No. 15/713,418 filed 22 Sep. 2017, now U.S. Pat. No. 10,231,614, which is a continuation-in-part of U.S. patent application Ser. No. 15/162,300 filed 23 May 2016, now U.S. Pat. No. 9,788,714, which is a continuation-in-part of U.S. patent application Ser. No. 14/326,335 filed 8 Jul. 2015, now U.S. Pat. No. 9,370,302 filed 8 Jul. 2014. U.S. patent application Ser. No. 16/264,242 is also a continuation-in-part of U.S. patent application Ser. No. 13/749,873 filed 25 Jan. 2013. The entire disclosures of all aforementioned documents are incorporated by reference herein.

FIELD OF INVENTION

Embodiments of the invention(s) herein relate to systems and/or methods that use wearable face protection equipment (FPE) with eye tracking sensors to observe eye position and/or motion, pupil size, and/or eyeblinks and use these observations to measure ocular parameters such as saccades, vergence, head static smooth pursuit, head dynamic smooth pursuit, eye fixation and/or gaze, pupil size changes, and/or eyeblinks. These ocular parameter measurements can be used to assess or determine the human health condition, using the FPE. Examples of said human health conditions can include:
(a) performance for individuals with normal human health;
(b) neurologic conditions, such as traumatic brain injury;
(c) mental health conditions, such as cognitive impairment;
(d) biochemical health impairments, such as metabolic dysfunction;
(e) physiologic health impairments, such as fatigue; and/or
(f) behavioral health conditions, such as substance use impairment.

BACKGROUND

Face protection equipment (FPE) has traditionally been used to protect facial structures from contact activity. FPE refers to a category of personal protective equipment (PPE) designed to safeguard a person's face from various hazards, such as impacts, splashes, airborne particles, chemicals, flying debris, and other potential dangers. It is essential in a wide range of industries and activities, including construction, manufacturing, healthcare, laboratories, recreational pursuits, and particularly in contact sports or activities associated with potential impacts. Face protection equipment in this document and embodiments is comprised of face guards, face guard components, face shields, visors, eyeglasses, contact lenses, jaw guards, goggles, respirators, helmets, windshields, or any related worn technology which can protect the face, or part of the face, from hazards, like that of impacts.

The eyes and eye responses are often considered a window for assessing central nervous system function. Eye tracking can have significant value in assessing human health including neurologic conditions, mental health conditions, behavioral health conditions, physiologic impairments, and biochemical impairments. Determining abnormal health conditions or impairments early can offer early treatments to prevent symptoms, functional disabilities or used as a controller method for operating vehicles or other equipment safely.

There are reportedly 3.8 million sports-related concussions (also referred to as traumatic brain injuries or TBIs) which occur in the U.S. each year and more than half of this amount is never reported. There may be no one on the sideline to notice such an event, no resources to properly evaluate the individual with a head impact, or the individual simply did not report the event. Current methods of concussion assessment for those individuals suspected as having a concussion are also inadequate. In football, an average player will experience approximately 378 head impacts each season. Secondary concussions also pose a greater risk to the brain, functionally and anatomically, particularly if they occur near the timing of the previous concussion event. The younger a player is, the greater the permanent risk of injury to the brain with concussions. There are also over 250,000 emergency room visits of young individuals annually for head injuries from sports and recreation activities. Over 50 million Americans participate in team sports and all of them are at some level of risk of experiencing a concussion. Concussions from multiple head impacts can result in chronic traumatic encephalopathy (CTE), which often is associated with behavioral health impairments and has caused many professional players to commit suicides. Central nervous system (CNS) impairments can persist in individuals with TBIs long after the last traumatic episode. Even a mild TBI (mTBI), will result in oculomotor abnormalities and can cause visual problems, such as difficulty with visual fixation on a viewed object of interest. It has been demonstrated that neurologic conditions, such as traumatic brain injury, can produce measurable changes in one or more of the following ocular parameters: saccades, head static smooth pursuit, head dynamic smooth pursuit, vergence, eye fixation, and/or pupil size changes.

It has been estimated that 1 in 4 individuals will experience a mental health condition at some point in their lives from such impairments of depression and anxiety impairments. A significant number of military personnel may experience symptoms of mental health conditions during or after deployment. Approximately 14% to 16% of the US service members deployed to Afghanistan and Iraq have been affected by PTSD or depression. Athletes are commonly affected with mental health conditions. 60-65% of high school and college athletes suffer anxiety and stress. The demands and pressures of sports, as well as the physical and emotional toll of training and competition, contribute to the development of these conditions. Common mental health conditions that athletes may experience include a post-traumatic stress disorder (PTSD), attention deficit hyperactivity disorder (ADHD), and bipolar disorder. The unique stressors and demands of sports can sometimes exacerbate or trigger these conditions. Abnormalities of saccades, eye fixation, duration of eye fixation, blink rate, head static smooth pursuit, and head dynamic smooth pursuit have been associated with mental health conditions as well as disturbances of visual attention, visual navigation, visual perception, visual search and visual reasoning.

Behavioral health conditions are often manifested as patterns of behavior that deviate from social norms or interfere with daily functioning. There is a very high correlation between substance use and behavioral health conditions. Behavior health conditions can be characterized by the problematic use of substances (e.g., alcohol, drugs), leading to the negative behavioral and health consequences. It has been reported that 70% of all adults with substance use impairment are employed and this substance use can affect jobs/play activity, safety, health, and liability.

Biochemical impairments are common, resulting in metabolic dysfunction, such as diabetes, enzymatic deficiencies, such as lactose intolerance, hormone abnormality, such as thyroid dysfunction or diabetes mellitus, nutritional deficiencies, such as iron deficiency which affects hemoglobin, as well as those proteins and other chemicals adversely affected by organ dysfunction. It has also been documented that biochemical health impairments caused by metabolic dysfunctions (associated with dehydration, renal failure, and diabetes), and pulmonary impairments (resulting in hypercapnia or hypoxia), can cause measurable changes in one or more ocular parameters including: saccades, head static smooth pursuit, head dynamic smooth pursuit, vergence, pupil size changes, eye fixation, and/or eyeblinks.

Physiological health impairments are very common in civilian and military populations. For example, impairments such as fatigue are common among athletes, with a reported incidence of 40% to over 80%, depending on the sport, training schedules, as well as other factors. This results in impairments of both physical and cognitive performances, and increased injury occurrence. Additionally, it has been demonstrated that physiologic health impairments such as fatigue can cause measurable changes in one or more of the following ocular parameters: pupil size changes, saccades, eye fixation, and head static smooth pursuit and head dynamic smooth pursuit.

Measures of eye movements, eye responses, eye positions and/or eye components (such as pupil size changes and eyeblinks) can be used to assess each of the health conditions accurately. Each of the aforementioned human health conditions can affect different areas of the neurologic system and each of the ocular parameters to be measured can assess different anatomical regions and neural pathways of the brain. Human health conditions and certain health disorders or impairments may be more accurately assessed by different ocular parameter measurements or by using a combination of ocular parameter measurements.

Historically, human health has been assessed in a clinical setting. New sensors and electronic technologies enable the development of portable systems for non-clinical environments. Such advancements facilitate increases in speed and accuracy for eye position and movement observations to measure ocular parameters such as saccades, vergence, head static smooth pursuit, head dynamic smooth pursuit, gaze, eye fixation, pupil size and/or eyeblinks. These ocular parameter measurements can more rapidly and accurately assess the human health condition for individuals participating in contact sports or other activities with risks of various hazards, including head impacts.

It is desired to overcome limitations of the prior art by using eye-observation-based systems and/or methods to assess human health through the use of enhanced face protection equipment (FPE). Desired outcomes include:

(a) Achieving a sufficiently high scan rate (also known as frame rate) so that high frequency movements (such as microsaccades) are captured;
(b) Improved accuracy;
(c) Higher resolution of the detected eye position and movement;
(d) Portability;
(e) Earlier detection (on-the-field and in real-time);
(f) Incorporation of artificial intelligence and machine learning;
(g) Aid in rehabilitation;
(h) Unobtrusiveness with activities;
(i) Transmission of data remotely and with telemedicine;
(j) Reduced physician visits;
(k) Remove disparity and have greater inclusivity;
(l) Lower healthcare cost; and
(m) Ability to be operated and used with minimal or no training.

Potential benefits of the face protection equipment (FPE) described herein can include changes in the standards of care and clinical recommendations by optimizing rapid evaluation and treatment. Ocular parameter measurements can be used to assess different areas of the central nervous system and different factors of the human health condition. Such systems and methods can function as health care provider and/or athletic trainer extenders by detecting abnormalities, monitoring the recovery process, and establish rehabilitation programs to speed up recovery. Such technology and methods can assess a human health condition, detect abnormalities or impairments, define the characteristics of the disorder, quantify the deficit, and wirelessly transmit this information remotely to another device. If an abnormal ocular parameter is noted for users participating in contact sports or other activity, rehabilitation can begin earlier and decisions regarding the need for extraction or returning to play or a previous work activity can be determined.

BRIEF DESCRIPTION OF THE DRAWINGS

The present invention will be better understood on reading the following detailed description of non-limiting embodiments thereof, and on examining the accompanying drawings, in which.

Figure 1:
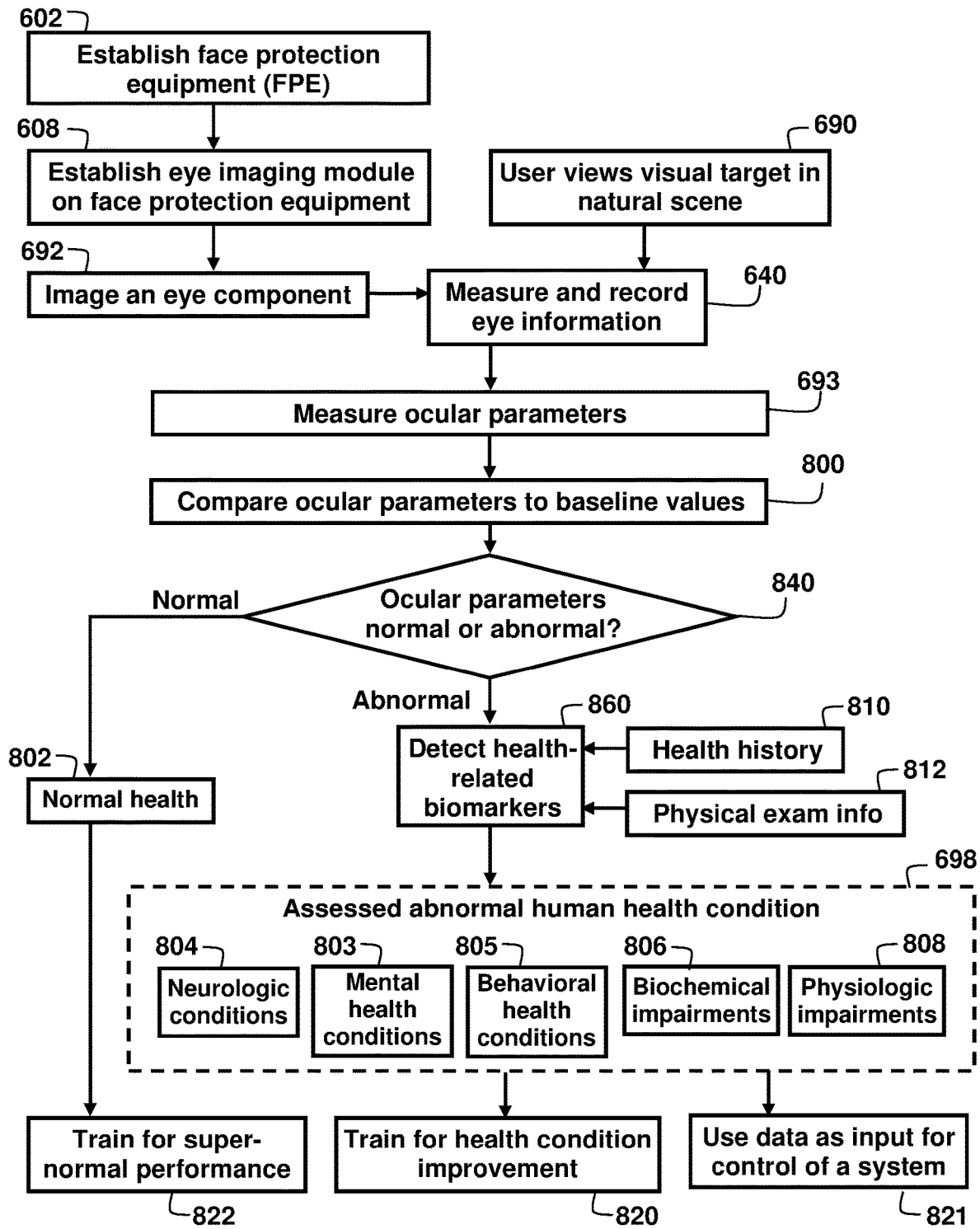
FIG. 1 is a method for using face protection equipment (FPE) to measure ocular parameters and assess health.

It should be understood that the drawings are not necessarily to scale. In certain instances, details that are not necessary for an understanding of the invention or that render other details difficult to perceive may have been omitted. It should be also understood that the invention is not necessarily limited to the embodiments illustrated herein.

DETAILED DESCRIPTION

The ensuing description provides preferred exemplary embodiment(s) only, and is not intended to limit the scope, applicability, or configuration of the disclosure. Rather, the ensuing description of the preferred exemplary embodiment(s) will provide those skilled in the art with an enabling description for implementing preferred exemplary embodiment(s). It should be understood that various changes could be made in the function and arrangement of elements without departing from the spirit and scope as set forth in the appended claims.

Specific details are given in the following description to provide a thorough understanding of the embodiments. However, it will be understood by one of ordinary skill in the art that the embodiments may be practiced without these specific details.

In one embodiment, the present invention uses at least one eye imaging sensor located on face protection equipment (FPE) to assess human health during an activity subject to head trauma or other hazards. The eye imaging sensor or sensors could measure eye movement (including saccades), eye position, pupil size, eyeblinks, and/or other eye information in individuals participating in sports or other activities. The human health condition being assessed could be a neurologic condition, a mental health condition, a behavioral health condition, a biochemical impairment, a physiologic impairment, or normal health. The FPE could protect a person's face from hazards and could specifically detect a concussion (TBI) when playing a sport or participating in some other activity. This system could further comprise a power source and an electronic circuit. The eye imaging sensor(s), power source and electronic circuit can be attached or embedded into the FPE, or these items could be external. Embodiments of the invention could further comprise a forward-facing camera, which could be used for gaze assessment and visual fixation ability.

Abnormal human health conditions that can be assessed using ocular parameters include neurologic conditions, mental health conditions, behavioral health conditions, biochemical impairments, and physiologic impairments. The following table lists types of neurologic conditions, examples, and related ocular parameters that can be measured. Each of these impairments can affect different areas of the central nervous system.

| Neurologic condition type | Detail and examples | Measured eye parameters |
|---|---|---|
| Traumatic brain injury (TBI, commonly rereferred to as a concussion) | Blunt trauma concussion<br>Blast concussion<br>Diffuse axonal injury | Eye fixation, Pupil size<br>Head static smooth pursuit<br>Head dynamic smooth pursuit<br>Saccades, Vergence |
| Neurocognitive impairments | Alzheimer's, Parkinson's<br>Lewy Body Dementia<br>Frontotemporal impairments<br>Neuroviral impairments | Eye fixation<br>Head static smooth pursuit<br>Pupil size changes<br>Saccades |
| Cerebral inflammatory or autoimmune impairments | Multiple sclerosis<br>Guillain-Barré syndrome<br>Encephalitis, Meningitis | Head static smooth pursuit<br>Saccades<br>Vergence |
| Cerebrovascular (CV) impairments | Migraines, Stroke<br>Transient ischemic attack (TIA)<br>Vascular dementia<br>CV stenosis, CV aneurysms | Head static smooth pursuit<br>Head dynamic smooth pursuit<br>Pupil size changes<br>Saccades |
| Seizure impairments | Focal seizures<br>Generalized seizures | Eyeblinks |
| Neuromuscular impairments | Muscular dystrophy<br>Myasthenia gravis<br>Cerebral palsy<br>Dystonia | Eyeblinks<br>Head static smooth pursuit |
| Neurogenetic impairments | Tay-Sachs disease<br>Neurofibromatosis | Head static smooth pursuit<br>Eye fixation |
| Neurodegenerative impairments | Amyotrophic Lateral Sclerosis<br>Huntington's disease<br>Spinocerebellar Ataxia | Head static smooth pursuit<br>Eye fixation<br>Saccades |
| Neoplastic impairments | Brain tumors | Vergence<br>Head static smooth pursuit<br>Saccades<br>Eye fixation |

The following table lists types of mental health conditions, examples, and related ocular parameters that can be measured.

| Human health condition | Underlying health cause | Measured eye parameters |
|---|---|---|
| Mental health condition | Cognitive impairment | Head static smooth pursuit<br>Pupil size changes<br>Saccades, Eyeblinks |
| Mental health condition | Chronic traumatic encephalopathy (CTE) | Eye fixation<br>Head static smooth pursuit<br>Saccades |
| Mental health condition | Attention deficit hyperactivity disorder (ADHD) | Eye fixation<br>Head static smooth pursuit<br>Saccades<br>Vergence |

-continued

| Human health condition | Underlying health cause | Measured eye parameters |
|---|---|---|
| Mental health condition | Anxiety disorder | Head static smooth pursuit<br>Head dynamic smooth pursuit<br>Saccades, Eyeblinks |
| Mental health condition | Depression | Eyeblinks<br>Eye fixation<br>Head dynamic smooth pursuit<br>Pupil size changes |

The following table lists types of behavioral health conditions, biochemical health impairments, and physiologic health impairments and related ocular parameters that can be measured.

| Human health condition | Underlying health cause | Measured eye parameters |
|---|---|---|
| Behavioral health condition | Substance use impairment | Saccades<br>Head static smooth pursuit<br>Head dynamic smooth pursuit<br>Pupil size changes |
| Biochemical health impairment | Metabolic dysfunction such as electrolyte deficits or hormonal abnormalities (diabetes, etc.) | Head static smooth pursuit<br>Pupil size changes<br>Saccades, Eyeblinks |
| Biochemical health impairment | Pulmonary impairments such as increased $CO_2$ or decreased $O_2$ | Pupil size changes<br>Vergence<br>Saccades, Eyeblinks |
| Physiologic health impairment | Fatigue/lack of alertness | Eye fixation<br>Pupil size changes<br>Saccades, Eyeblinks |
| Physiologic health impairment | Spatial disorientation | Eye fixation<br>Head dynamic smooth pursuit<br>Saccades |
| Physiologic health impairment | Intracranial pressure impairments within the skull | Eye fixation<br>Pupil size changes<br>Saccades, Vergence |
| Physiologic health impairment | Dizziness related to labyrinthine impairments | Head static smooth pursuit<br>Head dynamic smooth pursuit<br>Saccades, Vergence |

As shown in the preceding tables, different human health conditions require different ocular parameter measurements to detect an abnormality. The ocular parameter being tested must involve the neurologic pathway which was affected by the impairment. Additionally, certain health conditions have characteristic ocular parameter abnormalities. Here are some examples:

a. Many mental health conditions such as attention deficit hyperactivity disorder (ADHD) have demonstrated abnormal saccades, impairments with smooth pursuit, eye fixation and vergence. These impairments with eye movement can be associated with poor reading skills.

b. While neuropsychological testing traditionally has been used to measure mental health performance and mental processing deficits, the cerebral influences on the ocular motor system provide another quantitative mental health deficit assessment method. Abnormal eye movements can precede detection of mental conditions before neuropsychological cognitive testing and can accurately assess different mental domains. Different mental health conditions can be readily apparent with abnormalities of saccades, head static smooth pursuit, head dynamic smooth pursuit, vergence, eye fixation, and pupil size changes when measuring ocular parameters.

c. Substance abuse is the primary underlying health cause for behavioral health conditions. This is associated with eye movement abnormalities. Individuals with alcoholism may exhibit changes in eye movements, including reduced pursuit tracking and saccadic alterations. Substance use impairment, caused by drugs and alcohol, are associated with poor mental function with assessment of verbal/visual memory, visuospatial functioning, psychomotor speed, visual search/navigation, attention, cognitive control, and overall IQ. Alcohol has been shown to have diverse effects, including decreased velocity of both saccadic and head static smooth pursuit eye movements, increased saccadic latency, and pupil size changes. Intoxication may result in slowed or uncoordinated eye movements. These effects contribute to impaired visual information processing, which reduces human performance skills which requires visual activity. Barbiturates have been reported to produce effects like alcohol, and the effects of benzodiazepines and opioids seem to be more limited but still substantial.

d. Biochemical impairments of hormones, electrolytes, metabolites, and gases can result in abnormal eye movements. For example, high cortisol can be the trigger for adrenal stress symptoms and related long-term health problems. Cortisol levels have a profound effect on our eyes and vision. Some of the symptoms that can occur include double vision, sensitivity to bright light, difficulty focusing up close, memory issues, and blurred vision. Loss of sodium and dehydration can lead to impaired vision, changes in the cornea and decreased brain volume, all which can also affect ocular parameter measures.

e. Physiologic impairments, such as fatigue and changes of the intracranial pressure within the skull can adversely affect ocular parameters.

Based on the foregoing, it should be apparent that wearable face protective equipment and methods that measure ocular parameters can be valuable for assessing human health.

Definitions

The definitions that follow apply to the terminology used in describing the content and embodiments in this disclosure and the related claims.

Artificial intelligence (AT) is defined in this document and embodiments as a computer system program which attempts to implement aspects of human-level intelligence, in which a machine can learn and form judgements to improve a recognition rate for information as it is used. AI can behave in ways that both mimic and go beyond human capabilities. AI-enabled programs can analyze and contextualize data to provide information or automatically trigger actions without human interference. Artificial intelligence technologies include a machine learning (or more advanced deep learning) technology that uses an algorithm that classifies/learns the characteristics of input data by itself and an elemental technology that simulates functions such as recognition or judgment, like the human brain. The elemental technology can include a visual comprehension technique for recognizing objects as in human vision. In this document and embodiments, artificial intelligence is used with multiple indicators provided by the history, physical exam, laboratory studies and multiple methods of measuring the ocular parameters, to assess the human health condition and determine whether the data is to be used for determining normal health, abnormal health conditions, impairments, training, treatment, or as a system controller for other applications.

The autonomic nervous system (ANS) consists of the sympathetic and parasympathetic branches, both of which play roles in controlling aspects of eye function. The sympathetic branch is responsible for the "fight or flight" response. This branch controls the dilation of the pupils (mydriasis) through the action of the dilator pupillae muscle. This dilation allows more light to enter the eyes and is associated with arousal and responses to low light conditions. The parasympathetic branch is responsible for the "rest and digest" response. It is responsible for the control of constriction of the pupils (miosis) through the action of the sphincter pupillae muscle. Pupil constriction occurs in response to bright light or when focusing on nearby objects. The ANS with the oculomotor system, have distinct roles in regulating different aspects of controlling eye function. For example, when you shift your gaze to look at a distant object, the oculomotor system coordinates the eye movements, and the sympathetic branch of the ANS contributes to pupil dilation to enhance visual sensitivity. Alternatively, when focusing on a nearby object or encountering bright light, the oculomotor system adjusts the eyes, and the parasympathetic branch of the ANS causes pupil constriction to reduce the amount of light entering the eyes. The ANS controlling pupil size may influence the amount of light entering the eyes and regulate visual sensitivity and adaptation to different lighting conditions, but it is not the primary driver of eye fixation. The oculomotor system which controls voluntary eye movements primarily controls eye fixation to maintain a stable gaze on a specific point. Assessment of pupil size changes associated with the ANS is valuable, as this can determine neurologic impairments, including TBI, behavioral health impairments, which occurs with substance use, and physiologic impairments, such as fatigue.

Behavioral health conditions are emotions and behaviors that impact overall physical health, such as lifestyle choices, habits, and adherence to medical treatments. This condition focuses on the actions an individual takes. In this document and embodiments this condition largely refers to substance use behaviors, where substance use entails the consumption of psychoactive substances, such as drugs or alcohol, for various purposes, including recreational, medicinal, or self-medicating reasons. The term encompasses the ingestion, inhalation, or injection of substances that can alter behavior.

Biochemical health impairment in this document and embodiments refers to impairment or dysfunction in the biochemical processes within the body that can impact overall health. Biochemical processes involve the production, regulation, structure, levels, or physical properties of the biological or chemical nature of hormones, immunoglobulins, electrolytes, gases, or metabolites. This would include proteins, carbohydrates, lipids, nucleic acids, the mechanisms of enzyme action, the chemical regulation of metabolism, the chemistry of nutrition, the molecular basis of genetics (inheritance), the chemistry of vitamins, energy utilization in the cell, and the chemistry of the immune response. Most biochemical diseases affect the brain, and many lead to mental health impairments, developmental delays, behavioral problems, or neurologic handicaps. For example, the brain requires certain levels of neurotransmitters to function. They are the molecules used by the nervous system to transmit messages between neurons, or from neurons to muscles. Biochemical health impairments associated with mental health impairments have included hormone abnormalities such as serotonin, dopamine, norepinephrine, and gamma-aminobutyric acid (GABA). The hypothalamic-pituitary-adrenal axis (HPA axis), is responsible for the release of various hormones, including cortisol, which regulate the stress response. Examples of biochemical impairments include, but are not limited to, hypoxemia, hypercapnia, and Addison's disease.

Cognition is defined as the mental action or process of acquiring, understanding, and using knowledge through thought, experience, and the senses. In this document it represents a component of the mental processes. It encompasses various aspects of high-level intellectual functions and activities such as attention, memory, knowledge, decision-making, planning, reasoning, judgment, perception, comprehension, language, and visuospatial function. Mental processes are defined as encompassing all information processing even at the subconscious level or as the ability to think and reason. Other related mental-processes are concept formation, pattern recognition, imagery, and problem solving. Measurements of human eye movements have been shown to provide information of cognition, mental processing, and mental health conditions.

Cognitive impairments are defined as any impairment, disease, or condition that significantly impairs cognition, as defined above, and cognitive function of the person to the point where normal functioning in society is impossible without treatment. These impairments are a category of the larger mental health conditions. Cognitive impairments include various disorders and impairments affecting cognitive functions including neurocognitive impairments, which are specific subset types of cognitive impairments which involves impairments in cognitive functions associated with brain structure and/or function. There are various causes of cognitive impairments including brain injuries, such as chronic traumatic encephalopathy, infectious diseases or other diseases of the brain, drugs, alcohol, lifestyle factors and abnormal metabolic and/or hormonal abnormalities. In this document and embodiments, cognitive impairments are a subset of mental health conditions. These impairments are commonly detected by ocular parameter measurements. Eye position and eye movement measurements can be used to assess cognitive impairments and provide key treatment approaches. Visual and cognitive processing occurs during eye fixations which makes vision-based testing, such as with ocular parameter measurements, vital as a sensitive approach in the initial evaluation of mental health conditions. For example, head static smooth pursuit, head dynamic smooth pursuit, gaze and eye fixation can be used to detect cognitive impairments or mental health conditions. Additionally, other major eye movement parameters, such as saccades, eyeblinks, and pupillary measurements can provide distinct information about cognitive effort in response to task demand. Measures of cognition can include analytic comparison of movements and/or positions between the eye movement and target status, or between the head and eye movement and target status.

A concussion is a traumatic brain injury that results in temporary loss of normal brain function. It is characterized by immediate and transient alteration in brain function, including alteration of mental health condition or level of consciousness, that results from mechanical force or trauma. Concussions can be caused by direct trauma to the head, such as from falling, getting hit or being in an accident. They can also occur because of rapid acceleration-deceleration of the head, such as in whiplash injuries or blast injuries, such as in a war zone. A concussion can affect memory, judgment, reflexes, speech, balance, and muscle coordination and is associated with abnormal ocular parameter measures. In this document, it is used interchangeably with traumatic brain injury (TBI).

Controllers in this document and embodiments refers to electronic components or electronic devices which can regulate, manage, control, or direct the operation of other components or systems. They include, but are not limited to vehicle controllers, engine controllers, power controllers, aircraft engine controllers, vehicle control system controllers, flight controllers, remote controllers (transmitters), drone controllers, guidance system controllers, onboard system controllers, command system controllers, launch controllers, memory controller, cloud controller, and wireless local area network (LAN) controller. Each controller can also be comprised of other component such as Integrated circuits that contain a processor core, memory, programmable logic, and other programmable input/output peripheral devices.

The cornea is the circular transparent layer that covers the pupil, iris and anterior chamber of the eye and is the anterior one-sixth of the fibrous layer of the eyeball. The cornea is noticeably more convex to the outside than the sclera and is a completely avascular structure. The cornea is horizontally oval, measuring 11-12 mm horizontally and 9-11 mm vertically. The average corneal horizontal diameter (white to white) is 11.71±0.42 mm. The cornea is convex and aspheric with an anterior curvature of 7.8 mm and posterior curvature about 6.5 mm. There is a gradual increase in thickness from central cornea to the periphery. Alteration in tissue thickness is due to increase in the amount of collagen in the peripheral stroma and the thickness is found to decrease with age. These corneal components can be used for eye tracking, as beams of light striking the cornea create a reflection (e.g., a glint). Numerous corneal reflections (glints) can offer high resolution imaging of the pupil and cornea.

Dynamic eye fixation is defined as the ability to fixate on a visual target of interest, which is in motion. Dynamic eye fixation involves a series of quick, involuntary eye movements called saccades, which are responsible for shifting the point of eye fixation from one location to another. Static eye fixation refers to the ability to fixate on a stationary visual target of interest. In normal human activities, when viewing objects in the visual field, the head has natural motion or has movement and we follow moving objects or observe stationary visual targets of interest, while we are in motion. When observing a visual object of interest, it is important to have a focused position of the eye on the visual object when these objects are stationary or in motion, and the head is in motion. Our ability to maintain dynamic and static eye fixation on these visual targets while we are in motion, performing our daily activities, can provide a measure of human performance.

Eye components in this document and embodiments are defined as the anatomic features or distinguishing components of the eye, including the sclera, cornea, limbus, iris, pupil, eyelid and retina. Each of these components can be imaged by an eye sensor and used to measure ocular parameters and each of the components can be used to determine the position, movement, orientation, and functional activity of the eye to assess the human health condition, such as performance for individuals with normal human health, neurologic conditions, physiologic and/or biochemical impairments.

An eye imaging module in this document and embodiments refers to a device that images features and/or components of the eye and eyelids to measures ocular parameters. These measurements can include eye movement, eye position, eyeblinks and pupil size. The eye imaging module can include any mechanical, digital, or electronic apparatus for recording, storing, or transmitting visual images. Examples include still cameras, video cameras, and scanners. The eye imaging module can comprise light sources (e.g., infrared light), lenses, prisms, mirrors, and other means for converting images or light paths, and detectors of the light. The means for converting the image or light path can be passive or could be active, an example would be a micro-opto-electromechanical (MOEM) system. The detector could be a photodetector (e.g., an opto-electric transducers) that convert optical signals into electrical signals. It could also be an array of electro-optical sensors, such as the charge conducting device (CCD) arrays found in some video cameras. Other types of imaging devices include CMOS imagers, single photon avalanche diode (SPAD) sensors, global shutter image sensors, single photon sensitivity sensors, high frame rate image sensors, high dynamic range vision sensors, low voltage and low power imagers, and imaging systems on a chip. This eye imaging device can integrate the sensors, processor, electronic circuitry, and external interfaces. In this document and embodiments, eye tracking, eye sensor, eye imaging module, and/or eye orientation sensor all represent an eye imaging device, and the terms may be used interchangeably to represent measurements of eye movement, eye gaze position at any given time, and measures of any of the eye features as described herein.

Eye tracking is defined as the process of measuring where we look, also known as point of gaze or gaze point. In one embodiment, a light source, such as near-infrared light, is directed towards the center of the eyes (pupil), causing detectable reflections in the pupil and cornea. The resulting reflections, the vector between the cornea and the pupil, can be tracked by an infrared camera. This is the optical tracking of corneal reflections, known as pupil center corneal reflection. The pupil provides information of gaze direction and glints inform eyeball location. These measurements can be carried out by an eye sensor or sensing device, such as an imaging device comprised of an opto-electric transducer that detects the position and movements of the eye and converts the light signal to an electric signal.

Eyeblinks are the action of closing and re-opening the eyes (e.g., eyelid movement). Eyeblinks are either voluntary, involuntary (such as a spasm), or reflex blinks (evoked by an external stimulus). A voluntary eyeblink involves cortical control. Blink patterns can be comprised of incomplete or partial blinks, prolonged eyelid closure time and short blink intervals. When the eyes are closed during a blink, there is no incoming visual information to process. Eyeblinks can indicate changes in attention, fatigue, and cognition. Specifically, eyeblink characteristics in this document include the frequency of eyeblinks or eyeblink rate, the amplitude, velocity of blinks, blink latency, and the duration of blinks which can be measured to detect different human health disorders or impairments. Eyeblink in this document is used as an ocular parameter measurement to assess eyelid performance and/or function and detect normal human health and human health abnormalities, such as a neurologic impairment, mental health condition, behavioral health condition, biochemical impairment, and/or physiologic impairment such as fatigue.

Eye fixations are periods during which the eyes remain relatively still and focused on a specific location in the visual field for a certain duration. Fixations occur when the eyes gather detailed visual information from a particular point in the visual field. During eye fixation, the eyes maintain a relatively constant gaze point. More specifically, it refers to a collection of relatively stable gaze points that are near in both spatial and temporal proximity.

Eye fixation points refer to the specific locations or areas in the visual field where the eyes come to a rest during fixations. Eye fixation points can be points or targets of interest, objects, or features in the visual scene that attract the viewer's attention. It is the stationary eye position between eye movements or saccades when observing a point target. Eye fixation points are crucial for clear vision and detailed visual processing because the eyes need to remain relatively still to gather detailed information from a specific area. During fixation, the eyes hold steady on an object, and thus eye fixation reflects attention to a stimulus and strongly correlate with task performance. Eye fixation is a static concept with most fixations lasting between 50-600 ms, but the amount of time spent on a specific fixation is dependent on both the task and stimulus. Because task performance is also correlated with effort expenditure, there is a link between eye fixation frequency and cognitive effort. Eye fixations are those times when our eyes essentially stop scanning about the scene, holding the central foveal vision in place so that the visual system can take in detailed information about what is being looked at. Eye fixation measurement includes the number of fixations, position measures, and duration of the fixation. Eye fixations are excellent measures of visual attention and visual fixation ability on an object of interest, while the head is stationary or in motion and in this document can be an accurate and predictable measure of human performance, performance for individuals with the human health condition.

Eyelid movement is defined as the motion of the eyelid (e.g., also called an eyeblink) to position the eyelid in a particular place. More specifically, it is related to the velocity of an eyeblink, the duration of the eyeblink, the amplitude, as well as the frequency of eyeblinks, and whether the eyeblink is voluntary, involuntary, or reflexive during the upward or downward motion to position the eyelid in a specific location.

Eyelid position is defined by its location and as being normal when in primary gaze (e.g., binocular fixation while looking straight ahead). For example, in the resting position the eyelid position may be open, partially open or closed. The upper eyelid is positioned about 1 to 2 mm inferior to the superior limbus. Measured in another manner, the normal upper eyelid position in an individual may be up to 5.5 mm above the mid-pupil (or center of the cornea).

Eyelids are thin folds of skin that cover and protect an eye. The eyelid is made up of several layers; skin, orbicularis oculi muscle (main protractor muscle which closes the eyelid), tarsal plate, levator muscle apparatus (which lifts the eyelid, exposing the cornea), and palpebral conjunctiva. The orbicularis oculi muscle helps with both voluntary closure (sleep) and involuntary closure (blink). The names "palpebral" (and "blepharal") also refer to the eyelids. The key function of the eyelid is to regularly spread the tears and other secretions on the eye surface to keep it moist, since the cornea must be continuously moist. The blink reflex protects the eye from trauma or foreign bodies and with each blink the cornea and conjunctiva are swept of debris and relubricated. Both the upper and lower eyelids have rich vascular supply and have many anastomoses between the upper and lower lid circulations. In this document and embodiments eyelid characteristics (which include eyeblinks) can be used to assess the human health condition, such as physiologic and/or biochemical impairments and/or neurologic impairments.

Face protection equipment (FPE) in this document and embodiments refers to gear or devices or item of personal protective equipment (PPE), which aims to protect the wearer's entire face (or part of it) from trauma, injury or hazards. In this document and the appended claims, face guards, components of face guards, jaw guards, face shields, visors, goggles, eyeglasses, contact lenses, helmets, and eye shields are used synonymously and considered facial protective equipment. Even worn augmented reality and virtual reality devices can protect a portion of the face and eyes and could be considered FPE. Components of face guards or FPE include materials used in the FPE, or attached to the FPE, attachment points, and sensors with electronic components to measure features of human health. These sensors can be comprised of eye imaging device or module, head tracking sensors, biochemical and/or physiologic sensors, forward-facing camera, electronic circuits, power source and/or processor. These FPE devices can be attached to a helmet, worn separately with the aid of other attachment methods, or not worn but is positioned in front of the face. Technically, face protection equipment can even be unattached to the body, but in front of the face, like that of a motorcycle windshield, which protects the face from debris, wind, impacts, and other elements. Additionally, an automobile windshield, boat windshield, or aircraft windshield also can also be considered face protection equipment, as it primarily protects the face from similar elements. Eye imaging sensors (e.g., module) can be attached to the FPE or a component within the structure of the FPE, to measure ocular parameters for the purpose of assessing or determining human health, such as the neurologic condition, mental health condition, behavioral health condition, biochemical or physiologic impairment.

Focused position of the eyes is defined as the position or orientation of the eyes to provide a clear image of a visual element, visual object, or target of interest on the fovea. In this document and embodiments, it is also referred to as eye fixation, gaze point or point of gaze during an eye fixation, to provide the highest quality of visual acuity. It is used as an important ocular parameter measure to assess the human health condition.

Forward-facing camera in this document and embodiments is a device that turns images into electronic signals. It can also be referred to as a scene camera, a front-view camera, a webcam, a surveillance camera, a collision-avoidance camera, a world-view camera, a dash-cam, or a body-cam. A forward-facing is oriented to record what is in front of a device or person, toward the surroundings. The forward-facing camera data could be integrated with eye imaging sensor data, which analyze the user's eye movements, to determine the direction of gaze.

Functional activity of the eye is defined broadly as the ocular parameters and other eye activity described herein, which provides visual function to maintain good visual acuity. Measurements of functional activity include the ocular reflexes, eye gaze position or gaze point, eye fixation, eye orientation, eye position, and movements of the eye including pupil size changes. This functional activity also includes eyelid movement (e.g. an eyeblink), which provides protection to the eye. Fundamentally, movements include, saccades, which abruptly change the point of eye fixation, head static smooth pursuit, head dynamic smooth pursuit, which keeps a moving stimulus on the fovea, vergence, which align the fovea of each eye with targets located at different distances from the observer, pupil size/movement changes, which controls the amount of light which reaches the retina and maximizes visual acuity, and eyeblinks, which protects and lubricates the eye. All of these functional activities ultimately are designed to maintain maximal visual acuity with daily activities. Measures of functional activity in this document and embodiments assess eye fixation ability, performance for individuals with normal human health, and can detect an abnormal health condition, such as neurologic conditions, mental health conditions, behavioral health conditions, biochemical impairments, physiologic impairments including cognitive impairments, fatigue as well as provide health-related biomarkers for early treatment, monitoring, visual training or rehabilitation for these abnormal conditions.

Gaze refers to the direction in which a person is looking. It is the ongoing orientation of the eyes in relation to the environment or a specific object being viewed. Gaze can be dynamic, involving shifts in direction as a person explores their surroundings or focuses on different objects. Gaze can also be considered as a vector that indicates the line of sight from the eyes to a particular location. It encompasses various movements and involve a sequence of eye fixations on different objects as an individual visually explores their surroundings. A gaze point is the instantaneous spatial location of the visual axis landing on the visual stimulus. It refers to the specific location in a person's visual field where their eyes are directed at a particular moment. It is a snapshot of where the eyes are looking in terms of both an x and y coordinate and a timestamp corresponding to its measurement. Gaze points can change rapidly as a person looks around, scans a scene, or follows moving objects. The gaze point provides information about the current focus of attention. If a series of gaze points is very close, in time and/or space, this gaze cluster constitutes an eye fixation, denoting a period where the eyes are locked towards an object. Gaze can serve as a reliable indicator of attention and cognitive effort. In this document and embodiments, gaze and gaze point are important ocular parameter measurements in this human health system described herein for determining the human health condition.

Head dynamic smooth pursuit occurs when the visual target and head are both moving in the same direction, with the same angular velocity. The head rotates in the same direction as the motion of the visual target or object while the eyes remain fixed on the visual object of interest. The head dynamic smooth pursuit can be assessed with face protection equipment, with the systems and methods discussed in this document, using natural visual targets. In a preferred embodiment, dynamic smooth pursuit can assess the human health condition, including neurologic conditions like TBI, biochemical impairments, which occurs with metabolic dysfunction, and physiologic impairments, such as dizziness, because such impairments affect specific anatomic regions and neural tracts and pathways of the brain related to head dynamic smooth pursuit. The eye-tracking data can be analyzed to assess performance ability for participants to track the moving object while their heads move naturally in the same direction in real life applications, also knowing that head movements can affect eye movements. While this method doesn't measure head movements directly, it can provide valuable insights into how the eyes respond to a moving object.

Head static smooth pursuit is defined as the voluntary movement of the eyes in response to tracking a moving visual object, while the head is motionless. Such movements are under voluntary control in the sense that the observer can choose whether to track a moving stimulus. These movements are described to be smooth, continuous, conjugate eye movements with velocity and trajectory, determined by the moving visual target. However, the eyes are in continual small-scale motion, showing irregular drift and tremor, interspersed by miniature saccadic movements (less than 0.5 degrees). With the naked eye, head static smooth pursuit movement appears smooth, but with high-speed eye imaging devices, the movements are not entirely smooth at all, but can have an altered appearance due to the presence of saccades (covert or overt) or saccadic intrusions which can be associated with underlying neurologic conditions, or other physiologic or biochemical impairments. There are separate mechanisms of control for horizontal and vertical head static smooth pursuit tracking. Head static smooth pursuit eye movement can be divided into two stages: open-loop pursuit and closed-loop pursuit. Open-loop pursuit is the visual system's first response to a moving object and typically lasts approximately 100 msec. Therefore, this stage is ballistic and visual signals have not yet had time to correct the ongoing pursuit velocity or direction. The second stage of pursuit, closed-loop pursuit, lasts until the pursuit movement has ceased. This stage is characterized by the online correction of pursuit velocity to compensate for retinal slip. In the closed-loop phase, the eye angular velocity and target angular velocity are nearly equal. Pursuit eye movements are initiated within 90-150 msec, while typical latencies for voluntary saccades are in the order of 200-250 msec. The first 100 msec of pursuit is open-loop, and during this period no visual feedback is available because of the delays in the visual system. Thereafter, visual feedback is available to close the loop, and other sources of information are also available to improve performance. These movements are slower tracking movements of the eyes, designed to keep the moving viewed stimulus on the fovea. Measures of initiation parameters can detect information about the visual motion processing required for pursuit. When a bright light appears in the periphery, the fastest it can achieve a head static smooth pursuit is 30°/second. It first fixes the gaze to the peripheral light and, if not more than 30°/second, will follow the target equally with the movement. Head static smooth pursuit is an important ocular parameter measurement for assessing neurologic conditions, mental health conditions, behavioral health conditions, biochemical impairments, and/or physiologic impairments. Static smooth pursuit can also be accurately measured with face protection equipment with the systems and methods discussed in this document, using natural visual elements. Measurements of head static smooth pursuit ocular parameter include acceleration, accuracy, latency, and velocity.

Head static smooth pursuit acceleration refers to the rate of change of the eye velocity. The first approximately 20 milliseconds of pursuit tend to be the same regardless of target parameters. However, for the next 80 milliseconds or so, target speed and position have a large effect on acceleration.

Head static smooth pursuit accuracy is defined by the ability of the eyes to closely follow a moving object. The pursuit of visual targets moving with velocities of greater than 30°/s tends to require catch-up saccades. Head static smooth pursuit accuracy represents how closely the percentage of time the smooth pursuit velocity value remains within the target velocity value.

Head static smooth pursuit latency is defined by the time from target appearance to the beginning of pursuit. It is measured from traces of eye velocity. It is often calculated by finding the intersection between two regression functions, one fitted to velocity about the time of target appearance, and the second fitted over the initial part of the pursuit response.

Head static smooth pursuit velocity refers to the speed of the eye movement (velocity) which usually rises to a peak, following pursuit initiation, and then either declines slightly or oscillates around the target velocity. This peak velocity can be used to derive a value for gain (peak velocity/target velocity). It is usually near the velocity of the target. Instead of using peak velocity, measures of velocity at times relative to either target appearance or pursuit initiation can be made. For example, eye velocity up to 100 milliseconds after target appearance can be used as a measure of prediction or anticipation.

Health-related biomarkers are broadly defined in this document and embodiments as an objective, accurately measurable and reproducible ocular parameter indicator of an individual's medical signs or conditions. They are components, products, or processes of the body that can be objectively measured and evaluated as an indicator of biological or physiologic processes. In this document and embodiments, biomarkers represent the signs and features of neurologic conditions, mental health condition, behavioral health conditions, biochemical impairments, and/or physiologic impairments that can be detected by measured ocular parameters. These biomarkers can serve as early warning systems for health and may be a single characteristic or a panel of multiple characteristics. A biomarker can represent a measured ocular parameter indicator of pharmacologic, physiologic, or biochemical responses to a therapeutic intervention, including training, visual rehabilitation and/or pharmacological therapeutics. Changes in ocular parameter biomarkers can be a useful predictor of pharmaceutical treatment outcomes. As an example, abnormal vergence measurements in combination with abnormal head static smooth pursuit accuracy can be a biomarker for traumatic brain injury. A biomarker in Alzheimer's disease can be decreased amplitude and latency of the pupillary light reflex with increased pupillary size. Another example as seen in Parkinson's disease can be reduced saccadic accuracy and increased saccadic latency. A biomarker for chronic alcohol use can be prolonged latency with antisaccade tasks. Increased eye tracking sampling rates facilitate the specificity of biomarkers for particular disorders and impairments. Those specific disorders and impairments, such as neurologic conditions, biochemical impairments and/or physiologic impairments, can have distinct saccade components of accuracy, amplitude, latency, duration, and velocity, including those with antisaccade and prosaccade tasks. Additionally, these disorders and impairments can have distinct pupil size components of latency, velocity, amplitude, and duration. Vergence biomarkers of convergence and divergence measures including peak velocity, amplitude, symmetry, and latency can also be used to determine specific disorders and impairments. Conversion of an abnormal ocular parameter biomarker to a normal ocular parameter, following pharmaceutical therapy, can provide an accurate and valuable indicator of drug response, and such measurements can be used to assess therapeutic intervention, Human health condition is a multidimensional concept, requiring multiple indicators and multiple methodologies for adequate measurement. It represents an individual's level of wellness and illness, mentally and physically, and in this document and embodiments takes into account the measures to assess the presence of neurologic, biochemical and/or physiological health and function, mental and behavioral health, as well as performance for individuals with normal human health. It can be based on the individual's medical history, physical examination, assessment of laboratory studies, medications, existing disorders, impairments, or disabilities.

Human performance in this document refers to the effectiveness, efficiency and ability with which an individual can carry out tasks and activities. Components of human performance with activities include physical capabilities, cognitive abilities, motor skills with coordination of physical movements, mental, behavioral, and psychological factors. Physical and mental health and overall well-being are fundamental to human performance.

Internal body medical imaging is the technique or process of imaging the interior of a living organism for clinical analysis and/or medical intervention. Examples include 2-dimensional radiography, x-ray computed tomography (CT), magnetic resonance imaging (MRI), nuclear medicine such as PET scanners, medical ultrasound imaging, elastography, photoacoustic imaging, echocardiography, functional near-infrared spectroscopy, and magnetic particle imaging.

The iris is the colored ring portion of the eye. It is comprised of muscles microvessels, pigment cells and connective tissue. The color of the iris and other components are unique to each individual. The muscles of the iris control the pupil diameter and the amount of light entering the eye and the pigment of the iris serves to block out light, allowing it to only enter through the pupil opening. The iris muscle folds like an accordion when the pupil expands. Because of this accordion-like movement when the pupil constricts, the pleated folds can easily be visualized and in the pleats, the micro-blood vessels that nourish the iris are seen as very small white lines. The radius of the iris is 12 mm on average. The iris is divided into two major regions: the pupillary zone is the inner region whose edge forms the boundary of the pupil, and the ciliary zone is the rest of the iris that extends to its origin at the ciliary body. The collarette is the thickest region of the iris, separating the pupillary portion from the ciliary portion and where the sphincter muscle and dilator muscle overlap. The rich texture of the iris, including the presence of patterns, edges, or other complex features, unrelated to color are all important components of the image. In addition to light regulation, the human iris responds to emotional stimuli. cognition, sleep, and arousal. The iris components can be imaged by an eye sensor and used to measure ocular parameters to determine the position, movement, orientation, and functional activity of the eye to assess the human health condition, such as performance for individuals with normal human health, neurologic impairments, physiologic and/or biochemical impairments. Because of the uniqueness of the iris with each individual, scanning iris components can act as a controller to open and operate an electronic device or wearable device and establish or determine which ocular parameter testing or training programs are needed, based on the private information stored in a personal health database.

The limbus is the junction of the white opaque sclera and transparent cornea (e.g., corneal border) and is approximately 1.5 mm wide. Components of the limbus also contains vessels, the anterior ciliary arteries, and important features related to eye functions including fibrovascular ridges radially oriented known as palisades of Vogt that host corneal stem cells for epithelial turnover. The limbus is not symmetrical. The distance from the center of the eye to the upper limbus is shorter than for the remaining sectors. The mean range in horizontal meridian amounts to 12.68 mm and in vertical meridian 11.76 mm. Limbus components can be scanned as image features for eye tracking. The limbus can be imaged by an eye sensor and used to measure ocular parameters to determine the position, movement, orientation, and functional activity of the eye to assess the human health condition.

Machine Learning is defined as the science of getting computers to learn and act like humans, and improve their learning over time in autonomous fashion, by feeding them data and information in the form of observations and real-world interactions. Machine learning fundamentally is the technologies and algorithms to parse data, automatically learn insights and recognize patterns from data, and applying that learning to make increasingly better decisions. This entails getting computers to act without being explicitly programmed and is based on algorithms that can learn from data without relying on rules-based programming. Deep learning, an advanced method of machine learning, goes a step further. Deep learning models use large neural networks—networks that function like a human brain to logically analyze data, to learn complex patterns and make predictions independent of human input. Examples of machine learning in embodiments herein can include, but not limited to artificial neural networks, association rule learning, Bayesian networks, classifer learning, decision tree learning, deep learning, inductive logic programming, regression models, reinforcement learning, representation learning, rule-based machine learning, similarity and metric learning, and sparse dictionary learning.

Mental Health refers to an individual's emotional, psychological, and social well-being. Mental health conditions refer to mental illnesses or impairments which affect a person's thoughts, emotions, behavior, or a combination of these aspects. These conditions can significantly impact an individual's daily functioning, relationships, and overall well-being. Mental health conditions are diverse and can range from relatively common conditions, such as anxiety, depression, post-traumatic stress disorder (PTSD), attention-deficit/hyperactivity disorder (ADHD), and in this document and embodiments includes cognitive impairments.

Metabolic dysfunction refers any abnormality, disturbance, or impairment in the normal operation of metabolic processes. These processes are comprised of chemical reactions that occur within humans to maintain life. These processes are essential for the growth, development, energy production, and maintenance of the structure and function of cells. It includes those abnormalities, disturbances, or impairments which negatively alters the body's processing and distribution of enzymes, hormones, macronutrients such as proteins, fats, carbohydrates or impaired organelle function involving human organ systems. An example of metabolic dysfunction is a hormone abnormality like that of diabetes mellitus.

A neurocognitive impairment is a neurologic condition defined as an impairment in the cognitive function due to an underlying neurologic or medical disease or impairment affecting the structure or function of the brain. It includes those cognitive impairments due to Alzheimer's Disease, Parkinson's Disease, Huntington's Disease, Lewy Body Dementia, frontotemporal impairments and neuroviral associated impairments. It represents underlying brain pathology that results in a loss in cognitive abilities such as memory, problem solving, executive function, intellect, and perception. In this document and embodiments, it represents a subset under the broader category of cognitive impairments but seen with brain disease or impairments of the central nervous system.

A neurologic condition is defined in this document and embodiments as an impairment or condition that affects the brain, the spinal cord and/or nerves found throughout the human body, resulting in physical dysfunction. Structural, biochemical, physiologic, or electrical abnormalities in the brain, spinal cord or other nerves can result in a large range of symptoms.

Ocular Parameters are measurable factors that determine the components, actions, processes, behavior and functional ability of the eye, eyeball, and eyelid. Included in ocular parameters are eye position, eye and eyelid movement responses which can be detected or measured, including saccades, vergence, head static smooth pursuit, head dynamic smooth pursuit, pupil size, eyeblinks and the focused eye position (e.g., eye fixation). Reflexes included in the measured ocular parameters or eye movement responses include the pupillary light reflex, pupillary dark reflex, near accommodative triad, corneal reflex, blink reflex, and palpebral oculogyric reflex (Bell's reflex). The purpose of having eye movements is to maintain constant foveation of an object of interest or to foveate a target quickly. Measuring movements of eye includes the extraocular muscles (which move/rotate the eye), the ciliary muscles (which helps to focus by changing the lens shape), the levator (which raises the eyelid), and the pupillary muscle (which dilates or constricts the pupil).

Ocular reflexes are involuntary responses that are usually associated with protective or regulatory functions They require a receptor, afferent neuron, efferent neuron, and effector to achieve a desired effect. Examples of an ocular reflex include pupillary reflex, and corneal reflex.

Oculomotor system is defined as the part of the central nervous system (CNS) centers, complex CNS connections or pathways, numerous peripheral inputs, cranial nerves III, IV and VI and the extraocular muscles, which functions mainly in maintaining visual stability, aligning, and controlling eye movements. It is made up of many brain areas that cooperate to stabilize images of interest on the high-acuity part of the retina. The oculomotor system, which controls eye movements, including vergence, works in coordination with other systems to achieve stable and accurate eye fixation. The integration of vergence with other eye movements, such as pursuits and saccades, ensures that the eyes work together effectively to track and fixate on objects in the visual field. Assessment of impairments in oculomotor function is useful to detect visuomotor impairments due to a closed head injury and other neurologic and mental health conditions, as well as biochemical and physiologic impairments.

An opto-electric transducer is defined as a device that converts an optical signal into an electrical signal. Examples of such a device include photodetectors, photosensors, charge conducting devices (CCDs), complementary metal-oxide semi-conductor devices (CMOS), micro-opto-electro-mechanical-systems (MOEMS), microelectromechanical system (MEMS), and photodiodes.

Performance enhancement in this document and embodiments is defined as activities to improve human capability to do a task and/or improve health. Performance enhancement can comprise visual rehabilitation and/or visual training. Performance enhancement can be applied to ocular parameters discussed herein, to achieve a normal human health condition or supranormal ability.

A photodetector is defined as a device that turns light into an electrical signal. This can be an opto-electric transducer which converts the optical signal into an electrical signal. Multi-element photodetectors can be used for imaging. A non-imaging photodetector is a device that turns light into an electrical signal but has too few elements to produce an image. Thus, a non-imaging photodetector might comprise only one light-sensing element that turns received light into a magnitude based on the intensity of the light received. A non-imaging photodetector might comprise two light-sensing elements that allow the detection of an edge, but not an image, and therefore can be called an edge-detection photodetector. A non-imaging photodetector might comprise a two-dimensional pattern of three or four photodetectors, that allow the detection of an edge in more than one dimension, but not an image. Photodetectors could work with visible light, they could work with invisible light (such as infrared or ultraviolet), or they could work with a combination of visible and invisible light.

Physiologic health impairment is defined as impairment of the normal biological functions of organs, tissues, or cells of humans. It also includes impairments affecting the vital functions, growth and development, the absorption and processing of nutrients, the synthesis and distribution of proteins and other organic molecules, and the functioning of different tissues, organs, and other anatomic structures, such as the pulmonary, cardiac, and neurologic systems. Examples of physiologic health impairments includes, but not limited to, fatigue, diabetes mellitus, abnormal intracranial pressure impairments, kidney disease, autoimmune impairments, motion sickness, dizziness, eye movement impairments, retinopathy, and visual impairments.

The pupil is the black opening located in the center of the iris of the eye that allows light to strike the retina. In optical terms, the anatomical pupil is the eye's aperture, or the size of the circular opening through which light passes. The pupil appears black because light rays entering the pupil are either absorbed by the tissues inside the eye directly, or absorbed after diffuse reflections within the eye. Pupil size is a typical characteristic of the pupil that can be measured. In this document and embodiments, pupil size can also be the same as pupil diameter. The diameter of the pupil can be modulated by light, cognition, sleep, drugs and arousal. Dilation of the pupil is known as mydriasis and contraction as miosis. The size of the pupil, measured as diameter, can be a symptom of an underlying disease. For example, pupils can become mydriatic, or dilate, in response to potential disease, drug toxicity, trauma, increased intracranial pressure, brainstem damage, or nerve damage to cranial nerve II and/or III. Additionally, chromatic pupil size changes can be valuable due to its capacity to preferentially separate outer retinal (rod and cone-mediated) and inner retinal (melanopsin) responses in a single, objective, non-invasive pupil measurement. Pupil center corneal reflection (PCCR) can be used as a method for eye tracking, in which the pupil and corneal reflections are measured. Using such measurements, the eye position, point of gaze, orientation, and eye movements can be determined with advanced mathematical analysis.

Pupil performance refers to the response of the pupil to a given stimulus, activity and/or human health condition. Pupil performance can be determined by measurements such as changes in pupil size, changes in pupil dilation, pupil response latency, and pupil response duration. Pupil performance measurement can be used to diagnose a neurologic condition. Pupil size changes provide clinical health-related biomarkers of many ophthalmic and systemic conditions.

Pupillary light reflex refers to an autonomic reflex that constricts the pupil in response to light, thereby adjusting the amount of light that reaches the retina. Pupillary constriction occurs via innervation of the iris sphincter muscle, which is controlled by the parasympathetic system.

Pupil size changes is defined in this document and embodiments, as the measures of minute fluctuations in pupil diameter, (e.g., pupil size) in response to a stimulus. This includes pupil movement features as a function of time, to assess pupil performance. Pupil measures includes movement features of pupil diameter, dilation information including acceleration, latency, duration of changes in size, amplitude changes, and constriction information also including latency, duration as well as amplitude changes. It also includes peak and average constriction velocity from the iris sphincter muscle as well as dilation velocities of the dilator pupillae muscle under numerous stimulus conditions, including dim pulse, dim step, bright pulse, bright step, bright red step, and bright blue step. A higher frame rate is desirable to determine time parameters with a higher precision and examine the time dependence of the phase between the pupil and other bio-signals. A higher spatial or linear resolution also can provide information of micro-fluctuations in pupil size. Pupil performance or pupil size changes, which results from measures of pupil size and other pupil features described in this document and embodiments, can be an important health-related biomarker.

Saccades are defined as rapid, ballistic movements of the eyes that abruptly change the point of eye fixation when gazing from one object to another (i.e., rapid changes in eye orientation). The eye movements between fixations are generally referred to as saccades. Like eye fixations, saccades are made up of multiple gaze points and they have a start and end point each with a timestamp. Measures can be made at which point saccades occurred in time and their duration. The saccadic system serves to change our gaze from one point to another. The purpose of saccades is to alter the gaze from one object of interest to another under effort of will (voluntary saccades), to alter the gaze to a sudden event in the periphery (reflex saccades), to correct small errors of eye fixation (fixational microsaccades), and to correct small errors in pursuit (catch-up or back-up saccades). Vision is disrupted during saccades, a phenomenon called saccadic omission. Saccadic omission occurs because of visual masking in which the image seen before the saccade tends to mask the image seen during the saccade. Retinal blur occurs as the images move rapidly across the retina because the retina has limited temporal resolution. Saccade parameters of measurement includes accuracy, amplitude, inhibition, latency, duration, velocity with initial acceleration and peak velocity, frequency, and number over time. These quantitative measurements of saccades are used to assess the function of the oculomotor system, to investigate the effects of drugs or lesions, and to aid diagnosis of neurologic impairments or locating brain lesions in the central nervous system.

Saccade accuracy refers to the eye's ability to quickly move and accurately shift from one target fixation to another. Accuracy refers to how well the calculated eye fixation location matches actual eye fixation location. This is expressed in degrees of visual angle (a half circle has 1800 of visual angle). Saccade adaptation is a process for maintaining saccade accuracy based on evaluating the accuracy of past saccades and appropriately correcting the motor commands for subsequent saccades. An adaptive process is required to maintain saccade accuracy because saccades have too short a duration relative to the long delays in the visual pathways to be corrected while in flight.

Saccade amplitude refers to the size of the eye movement response, usually measured in degrees or minutes of arc. The amplitude determines the saccade accuracy. This is sometimes referred to as gain. It is also described as the angular distance the eye travels during the movement.

Saccade Inhibition refers to an absence or near-absence of saccades initiated around 80-120 msec following a brief visual distracting effect that interferes with the production of scanning saccades.

Saccade latency refers to the time taken from the appearance of a visual target to the beginning of an eye movement in response to that target. Normal saccades have a latency of typically about 200 msec. Many factors influence saccade latency. Longer latencies occur with weak (dim or low contrast) targets, unpredictable targets, and with older individuals. Shorter latencies occur with brighter visual targets, predictable targets, with auditory stimuli, and with younger individuals.

Saccadometry is defined as the functional evaluation of saccadic eye movements with the neural pathways and frontal, parietal and occipital areas of brain involvement. Saccadometric measures can include accuracy, latency, duration, frequency, and velocity of a saccade or multiple saccades in combination with the position or movement of each eye. The two most common assessments are the prosaccade and anti-saccade. A prosaccade requires an eye-movement toward target jumps. Specifically, individuals are instructed to look at a center target and then need to direct their gaze toward a target dot appearing at the periphery as quickly and as accurately as possible. After viewing the peripheral target, they then return to the center target dot and wait for the next target jump. By contrast, anti-saccade tasks typically require an eye-movement of equivalent amplitude to be executed rapidly, but in the opposite direction. To achieve this, the natural tendency to move the eyes towards the new stimulus has to be overcome in order to direct a voluntary saccade in the opposite direction. The technology discussed herein and in embodiments can utilize saccadometry as a health-related biomarker to enhance the diagnosis and monitoring of neurological conditions, such as traumatic brain injuries.

Saccade velocity is defined as speed measurement during the eye movement. High peak velocities and the main sequence relationship can also be used to distinguish microsaccades from other eye movements such as ocular tremor and ocular drift. Saccades have a very high velocity, up to 800 or even 1000 degrees per second for very large saccades. Saccade velocities follow a very specific, predictable pattern such that the peak velocity of the saccade is dependent on its amplitude. Saccades are reprogrammed after each eye fixation period. In most cases, if a target moves during a saccade, the saccade in progress is not modified and the next saccade will not occur until one latency period after the end of the first saccade. Therefore, saccades have been called ballistic, meaning that they are determined before they are started and cannot be redirected during movement. Inaccurate control of saccades is termed saccade dysmetria, undershoots are referred to as hypometric and overshoots are termed hypermetric. Peaks corresponding to saccadic movements show a linear relationship between the peak velocity of a particular saccade and the amplitude. Once the peak velocity has been reached, the amplitude of the saccade, and therefore the final position of the eye after the saccade can be determined with a high degree of accuracy. Saccades have fixed relationships between the amplitude, duration, and peak velocity. There are main sequence parameters and relationships. Generally, in normal individuals there is a linear relationship between saccade amplitude and duration.

Sampling rate of eye tracking refers to how many times per second eye position is measured. Common sampling rates are 1,000 Hz, 500 Hz, 250 Hz, 120 Hz, 90 Hz and 60 Hz. During normal adult reading, eye fixation durations typically vary from about 100-800 milliseconds, with the average being approximately 250 milliseconds. Higher sampling rates produce better temporal accuracy when measuring the duration of eye fixations and saccades. Specifically, the average temporal error will be approximately half the duration of the time between samples. For example, a sampling rate of 1,000 Hz (sampling eye position every 1 millisecond) will lead to an average error of 0.5 millisecond and a sampling rate of 60 Hz (sampling eye position every 16.7 milliseconds) will lead to an average error of approximately 8 milliseconds.

The sclera is the white portion of the eyeball and its related blood vessels. Characteristically the sclera is comprised of the episclera, an outermost connective tissue layer which is connected superficially to the Tenon's capsule, and its deep surface which overlies the scleral stroma. The anterior part of the episclera also contains a plexus of blood vessels formed by the branches of the anterior ciliary arteries. This plexus is normally not visible, however during inflammation it becomes congested, giving the characteristic appearance of the 'red eyes' in the affected individual. It is the scleral stroma, composed of dense irregular connective tissue, which gives the sclera its distinctive white color. The change of scleral color can indicate a pathological process in the body; for example, a yellow sclera may indicate liver diseases such as hepatitis. Lamina fusca is the innermost layer of the sclera and receives its name from the large number of melanocytes. Reflections from light sources on the sclera can be used for eye tracking. A glint can be identified as a reflection of light from a sclera characteristic. Glints can be used to measure eye movement, orientation and position of the eye.

Slippage is defined as when an imaging device viewing a subject's eye moves out of phase with the subject's head. The slippage offset is an algorithm that can account for slippage and computes an appropriate value that can be used to synchronize sensor data.

Vergence is the ability of shifting our point of gaze from a far object to a near object, causing our eyes to converge. At the same time, the lenses of our eyes modify their focus (accommodate), and our pupils often constrict. The mechanism and control of vergence eye movements involves complex neurological processes that can be compromised in individuals with traumatic brain injury, resulting in a wide range of vergence dysfunctions and related near-work symptoms, such as oculomotor-based reading problems. Overall, vergence is an important component of the oculomotor system's role in maintaining eye fixation for both near and distant objects. To maintain binocular vision, the eyes must rotate around a vertical axis so that the projection of the image is in the center of the retina in both eyes. Vergence measurements can easily be performed. Normally, changing the focus of the eyes to look at an object at a different distance will automatically cause vergence and accommodation, known as an accommodation-convergence reflex. Convergence is the simultaneous inward movement or orientation of both eyes toward each other, usually to maintain single binocular vision when viewing an object more closely. Divergence is the simultaneous outward movement or orientation of both eyes away from each other, usually to maintain single binocular vision when viewing an object which is further away. Typically, vergence velocity responses do not exceed 60 degrees/second. Vergence orientation movements tend to have relatively long latencies, typically on the order of 150-200 msec. Measurements of vergence can be performed while visually following the target element of interest, which moves in a smooth transition to different depths (e.g., dynamic vergence) or in a sequence of steps with the head stationary or head in motion. Such measurements can also include a binocular precision index (BPI) and binocular accuracy index (BAI) to quantify changes of convergence and divergence peak velocity, amplitude, symmetry, and latency. Vergence can accurately be measured with face protection equipment with the systems and methods discussed in this document, using natural visual elements.

Figures Describing Ocular Parameter-Based Human Health Assessment

Referring now to the figures, FIG. 1 shows a generalized method for observing eye information to measure ocular parameters. These ocular parameters, in combination with other information, can then be used to assess human health. The resulting information can be used for health condition improvement or as input for control of a system.

The generalized method shown in FIG. 1 starts by establishing face protection equipment (FPE) as shown at 602. Next, an eye imaging device (e.g., module) 608 is established on the face protection equipment 602. The eye imaging module 608 is used to image an eye component, a step shown at 692. The eye component being measured in step 692 can comprise a retina, sclera, cornea, iris, limbus, pupil, or eyelid. In the embodiment of FIG. 1 and other embodiments described and illustrated herein, an infrared light source in the eye imaging module 608 could be used to improve measurement of the eye components. The user views a visual target in a natural scene, as shown at 690. The eye imaging module 608 images the eye component 692, and eye information is measured and recorded 640, in response to the users view of the visual target of the natural scene 690. The eye information that is measured and recorded in step 640 can comprise eye position information, horizontal eye movement information, vertical eye movement information, pupil size information, eyelid information (and more specifically eyeblink information), and any combination of this information or anything similar capable of being understood by anyone skilled in the art.

The eye information from step 640 can then be used to measure ocular parameters, as shown at step 693. Examples of ocular parameters that embodiments of the FPE invention can be configured to measure can include saccades (see FIG. 6), vergence (see FIG. 7), head static smooth pursuit (see FIG. 8), head dynamic smooth pursuit (also on FIG. 6), eye fixation and/or gaze (see FIG. 11), pupil size changes (see FIG. 9), and/or eyeblinks (see FIG. 10).

Further referring to FIG. 1, the ocular parameters measured in step 693 can be compared to baseline values (i.e., normal values), as shown at step 800, to determine if ocular parameters 840 are normal. If ocular parameters are abnormal, the ocular parameter information can be supplemented with physical exam information 812 and health history (which can comprise prior lab results, imaging, and vital signs) 810, to detect health-related biomarkers 860, which in turn can be used to assess an abnormal health condition, at step 698. This assessed human health condition 698 can be categorized into:

a) Performance for individuals with normal human health condition, shown at 802;
b) Neurologic conditions, such as traumatic brain injury (TBI), shown at 804;
c) Mental health conditions, such as cognitive impairment, shown at 803;
d) Behavioral health conditions, such as substance use impairment, shown at 805;
e) Biochemical health impairments, such as metabolic dysfunction, shown at 806; and
f) Physiologic health impairments, such as fatigue, shown at 808.

Regarding 810 (health history), diagnosis of a health condition has been described as both a process and a classification scheme, or a pre-existing set of categories agreed upon by the medical profession to designate a specific condition. The working diagnosis may be either a list of potential diagnoses (a differential diagnosis) or a single potential diagnosis. Generally, there are four types of information-gathering activities in the diagnostic process: 1) taking a clinical history and interview; 2) performing a physical exam; 3) obtaining diagnostic testing; and/or (4) sending a patient for referrals or consultations. A subject's clinical history includes documentation of the current concern, symptom history, past medical history, family history, social history, and other relevant information, such as current medications (prescription and over the counter) and dietary supplements. An accurate history facilitates a more productive and efficient physical exam and the appropriate utilization of diagnostic testing. The medical history of a patient is the most useful and important element in making an accurate diagnosis, much more valuable than either physical examinations or diagnostic tests. The medical interview is the process of gathering data that will lead to an understanding of the disease and the underlying physiological process.

Biomarkers (step 860) are important. It is biomarkers that enable us to distinguish Alzheimer's from Parkinson's, etc. and treatment related to early biomarker identification can prevent symptoms and enable more rapid recovery of impairments.

Further referring to FIG. 1, the assessed human health condition from 698 can be used to train for health condition improvement, as shown at 820. The training, treatment, and/or rehabilitation step shown at 820 is further described with reference to FIG. 12. A specific rehabilitative program could be used for treatment of the abnormality identified with the human health condition. Performance training for individuals with normal human health, using ocular parameters, can also be achieved for enhancement of activity skills (e.g., by improvement of eye fixation ability). Thus, embodiments of the inventions described herein can provide supernormal enhancement 822 of the ocular parameters discussed, where no balance impairment exists, for enhancement of athletic or vocational abilities. Embodiments can enable individuals to reach a higher level of performance in their occupation, enable them to have increased ocular performance functions when participating in their usual occupational or play activities as well as enabling cognitive training and rehabilitation.

FIG. 1 also shows that data from the generalized method for assessing human health condition could be used as input for controlling a system, as illustrated at step 821. One example of system control in step 821 might be the use of health condition information from step 698 to control a vehicle, and more specifically to determine whether the human, who has been assessed at 698, is capable of safely operating the vehicle.

When assessing mental health conditions numerous visual assessments can be performed while viewing visual targets. For example, ocular parameter measurements, including head static smooth pursuit, head dynamic smooth pursuit, pupil size changes and eyeblink information use visual targets for assessment, and all provide information about cognition and inattentiveness. There are other visual mental health function tests to detect cognitive impairments. These tasks can be used as visual mental health function assessments, that will be further described with reference to FIG. 13.

Figure 2:
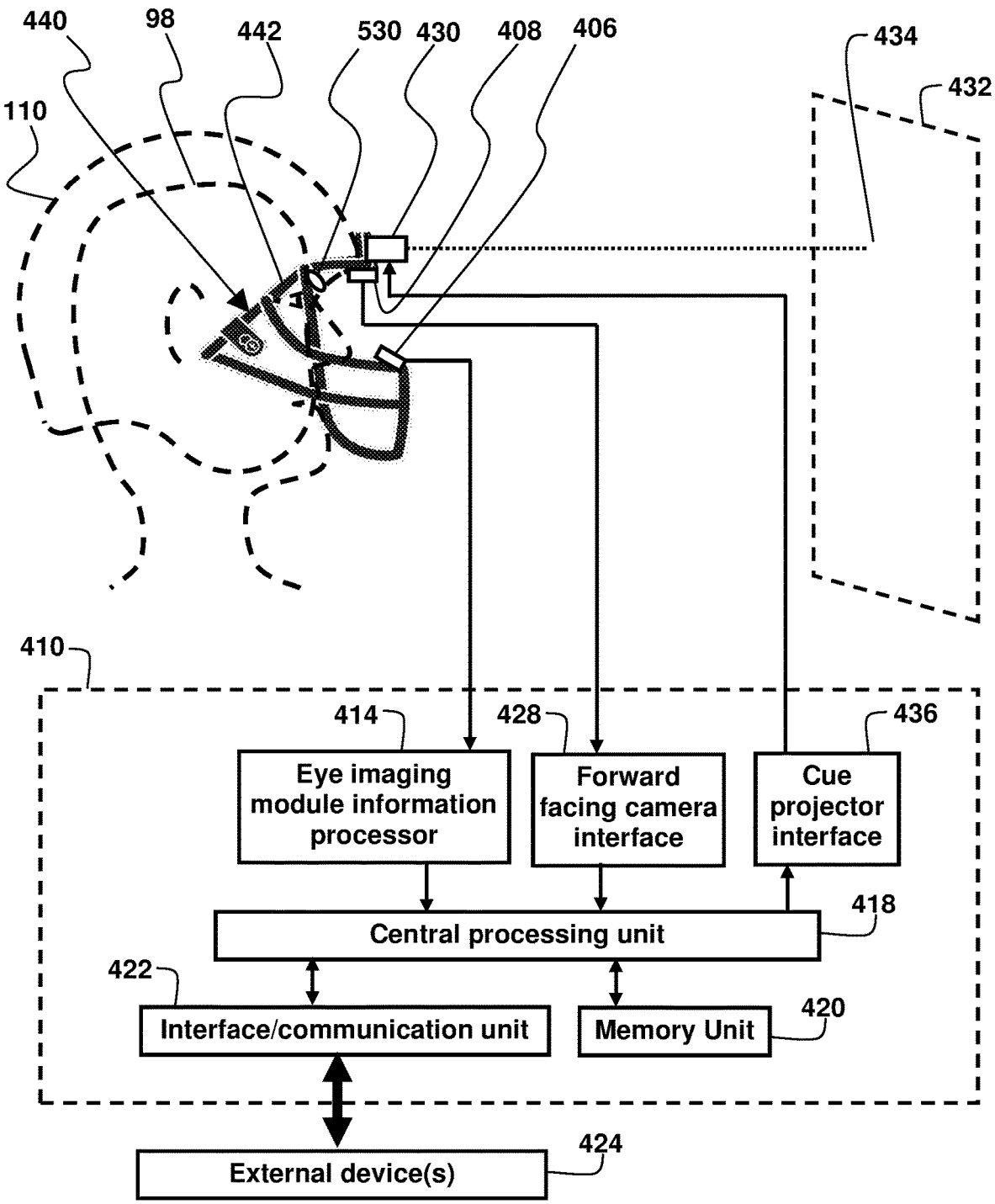
FIG. 2 shows a face guard that comprises an ocular performance measurement system.
Figure 3:
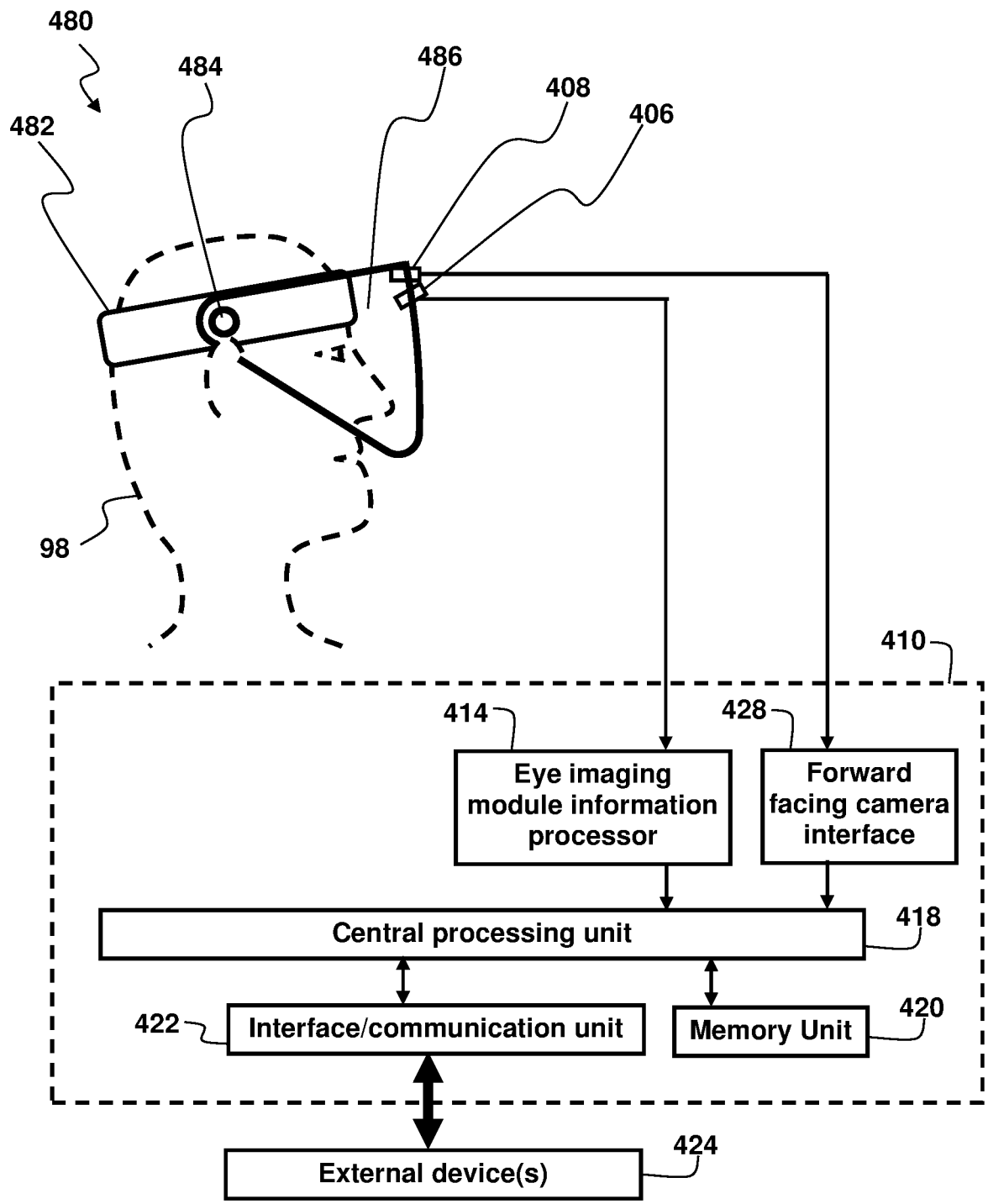
FIG. 3 shows a visor or face shield-based ocular parameter measuring system.
Figure 4:
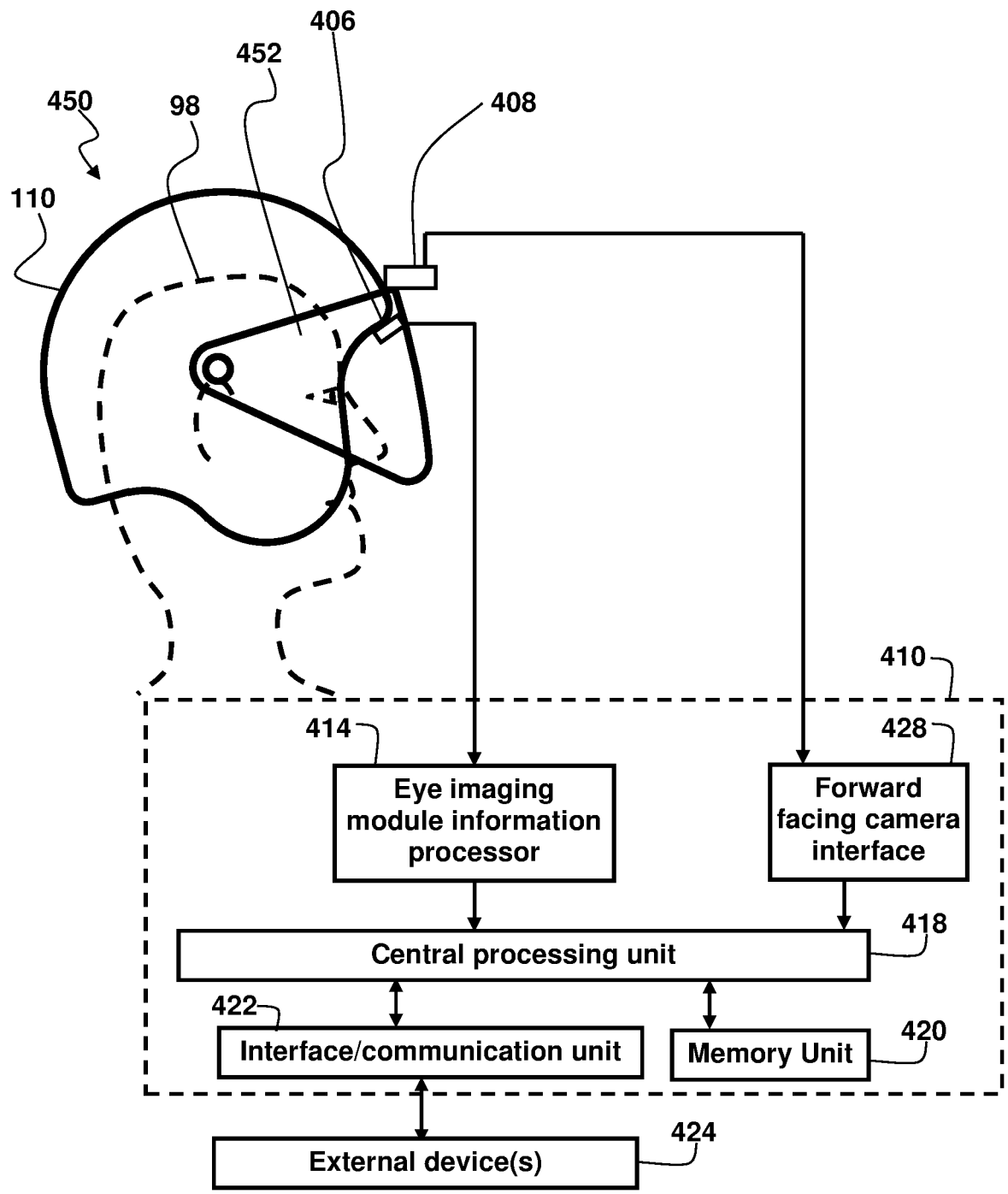
FIG. 4 shows a face shield that comprises an ocular performance measuring system.

FIG. 2, FIG. 3, and FIG. 4 illustrate examples of face protection equipment (440, 480, and 450, respectively) that comprise at least one eye imaging module 406 for imaging at least one eye component to measure and record eye orientation information, which can then be used to assess human health conditions, such as normal human health, neurologic conditions, mental health conditions, behavioral health conditions, biochemical health impairments, and physiologic impairments using the method that was shown in FIG. 1. In these systems any eye component could be imaged, such as a retina, a sclera, a cornea, an iris, a limbus, a pupil, and/or an eyelid. These systems could measure both eyes, allowing left eye information to be compared to the right eye information. The systems shown in FIG. 2, FIG. 3, and FIG. 4 can comprise any wearable face protection equipment of the types that will be further described herein. It should be recognized that the face protection equipment could also be non-wearable, examples of which might include a vehicle windshield.

FIG. 2 illustrates one example of a wearable faceguard-based ocular performance measuring system 440. In this embodiment, the faceguard frame is shown at 442, and is attachable to a helmet 110, to be worn on a person's head 98. The faceguard frame 442 could comprise a plurality of rigid structural members with at least one aperture for facilitating human vision through the faceguard. The faceguard frame 442, could comprise materials such as metal, carbon fiber, plastics, glass fiber, or any combination of these materials or others capable of being understood by anyone skilled in the art. The faceguard frame 442, could comprise eye sensing elements and/or transducers for detecting and measuring eye movements and circuitry to the electronic elements such as: an eye imaging module 406, connected to an eye imaging module information processor 414; and a central processing unit 418, memory unit 420, and interface/communication unit 422 for communicating with an external device 424. The electronic module 410, that comprises the eye imaging module information process 414, central processing unit 418, memory unit 420, and interface unit 422 could be located on the face protection equipment or externally. The eye imaging module 406 could image a left eye component and a right eye component. The system could comprise two eye imaging modules 406, one for imaging a left eye component and one for imaging a right eye component. In an embodiment, the eye imaging module 406 could simultaneously image a component from both eyes.

The faceguard-based system 440 of FIG. 2 could have other sensors that interface with the electronic module 410. As an example, the faceguard-based system 440, of FIG. 2 might have a forward-facing camera 408, that communicates with a forward-facing camera interface 428, in the electronic module 410. The forward-facing camera 408, could capture images or video frames of the external environment, including scenes, objects, or people in the user's surroundings (e.g., visual data information of the external environment). The visual data information could include light features of the environment which refers to the various characteristics and properties of light in a given setting. The data from the forward-facing camera and eye-tracking sensors could be integrated and processed by the central processing unit 418. Advanced algorithms could interpret the eye movements, correlate them with the visual data acquired from the world-facing camera, and calculate the user's point of gaze within the external environment. The eye imaging module 406 can be responsive to the visual data obtained from the forward-facing camera 408 to measure the ocular performance. The central processing unit 418, or the external device 424, could combine the information from the eye imaging module 406, and the forward-facing camera 408, to assess one of the ocular performance parameters described herein.

Further referring to FIG. 2, the faceguard-based system 440, could also have a forward-pointing visual cue projector, shown at 430. This visual cue projector 430, could comprise a light source, and that light source could comprise a light emitting diode (LED) or a laser. The light source can project a visual cue 434 (visual object or visual element) onto a surface 432. The surface 432 could be any available surface, examples of which might be an area of open or cleared ground nearby, or a subdued solid wall surrounding the field, positioned approximately 3 meters or 10 feet from the user. The user's ability to maintain his/her gaze on this projected cue 434 (visual object or visual element) on the surface 432 can be used for calibration or testing of the ocular parameter being measured. For example, the projected visual cue 434 could remain stationary when the user's head moves. The system could also be configured so that the visual cue 434 moves on the surface 432 and the user's ability to follow this movement is measured. The visual cue projector 430 could be controlled through a cue projector interface, shown at 436, that is part of the electronic module 410. The visual cue projector 430 could be responsive to the central processing unit 418.

In an alternative embodiment, the faceguard-based system could be an insert for a normal faceguard and could comprise the eye imaging sensor, power source and circuitry.

In another embodiment, sensors could be attached to the faceguard or other types of face protection equipment (FPE) for measuring the characteristics of an impact. These sensors can be located in preferred positions most likely to detect linear and tangential impacts, relative to the rotational center of the wearer's head. As an example, with head worn FPE, sensors used to measure linear impacts could be placed in the frontal or occipital area and tangential impacts could be placed in the lateral or temporal location.

Embodiments of the present FPE invention could be implemented with eye trackers (also described herein as eye sensors), shown for example at 406 in FIG. 2, which are not video cameras. Examples could include any eye imaging device as described previously, which includes any mechanical, digital, electromagnetic, or electronic apparatus for recording, storing, or transmitting visual images. In another embodiment, the eye sensor, 406, is an image sensor capturing single images or frames from the sensor greater than 60 frames per second. The system could also have an infrared illumination source 530 to facilitate the imaging performed by the eye imaging module 406.

The faceguard-based system 440 of FIG. 2 could have other sensors that interface with the electronic module 410. In an alternative embodiment, the faceguard system 440 of FIG. 2 could comprise a display (not shown) and a head orientation sensor (not shown) in addition to the eye imaging module 406. The display unit could be attached to the faceguard to provide visible images for ocular performance assessment as described herein. In another embodiment, the display (not shown) could perform multiple functions including: (a) providing the visual elements required for measuring the ocular parameters; and (b) an eye tracking video camera, all located within a display unit. This display could be any type of small portable electronic device. The display could have its own power source and could be configured for being responsive to other sensors, such as the forward-facing camera and/or impact sensors.

Features of the system and methods described herein could also be used in a face protection device embodiment, such as the face shield system shown at 480 in FIG. 3. In this embodiment, a head attachment member for the face shield is shown at 482 and is configured for attachment to a person's head 98. The head attachment member 482 could be rigid or flexible. The head attachment member 482 can be attached to a see-through shield 486 using pivotable or other linkages 484 on each side of the head attachment member 482 to allow the shield 486 to be rotated up out of the line of sight. The see-through shield 486, could comprise transparent or translucent materials. The face shield system 480 can comprise eye imaging elements and/or transducers for detecting and measuring eye position, eye movements, pupil size changes, and/or eyeblinks as previously described and circuitry to the electronic elements such as:
  (a) the eye imaging module 406, connected to the eye imaging module information processor 414; and
  (b) the central processing unit 418, memory unit 420, and interface/communication unit 422 for communicating with an external device 424.

The face shield-based system 480, of FIG. 3 might also have a forward-facing camera 408, that communicates with a forward-facing camera interface 428, in the electronic module 410. The eye imaging device 406 can be responsive to the visual data input from the forward-facing camera 408 to measure the ocular performance. In this case, the central processing unit 418, or the external device 424, could combine the information acquired from the eye imaging device 406, and the forward-facing camera 408, to determine one of the ocular performance parameters described herein. The face shield-based system could also comprise an illumination source. This illumination source could project infrared light, near infrared light, or visible light in the direction of the person's eyes to help improve the sensitivity of the eye imaging device 406 and make it less sensitive of other light sources, which may produce noise and/or glint.

FIG. 4 shows a face shield or visor embodiment of an ocular measurement system 450 comprising a face shield 452 attached to a helmet 110 configured for a human head 98. The face shield system can comprise eye imaging module 406 and a forward-facing camera 408 which could be coupled to the electronic module 410. The electronic module 410, could be part of the face shield system 450, or the electronic module 410, could be external to the face shield system 450, and communicate through a wired or wireless connection.

The electronic module 410 shown in FIG. 4 can comprise an eye imaging module information processor 414, a forward-facing camera 428 interface, a central processing unit 418, a memory unit 420, and an interface and/or communication unit 422 as shown and configured in FIG. 4. The electronic module 410 can be configured to communicate with an external device (or devices) 424 using any of the methods and systems described herein.

Further referring to FIG. 2, FIG. 3, and FIG. 4, the forward-facing camera 408, can be configured to adjust its field of view, focal length, or to zoom in or out in response to an eye sensor. The electronic module 410, using the central processing unit 418, could control the forward-facing camera 408. This control of the forward-facing camera 408, could be through wired or wireless electronic signals. The forward-facing camera 408, could transmit video information to the electronic module 410, and this video information could be analog or digital information and could be transmitted through a wired or a wireless connection. The information collected and/or recorded by the forward-facing camera 408, could also be used for capturing visual images of the user's surroundings, or activate a photo or video feature and determine the intended gaze point of the user. The camera can be used to identify, track specific viewed targets or objects in the scene and facilitate input for various applications such as navigation, gaming and mapping the environment. It can also function as a method to capture and analyze the user's eye movements, monitor the position and/or gaze direction of the eyes (e.g., gaze tracking). As discussed previously, the determined intended gaze point can be measured and correlated with the eye fixation accuracy of the eye tracking sensors. The user can also perform a predetermined action with the eye(s) by focusing on a specific image or orienting the eye in a specific manner as an input control. Data collected can be uploaded and transmitted to a remote or external device.

Figure 5:
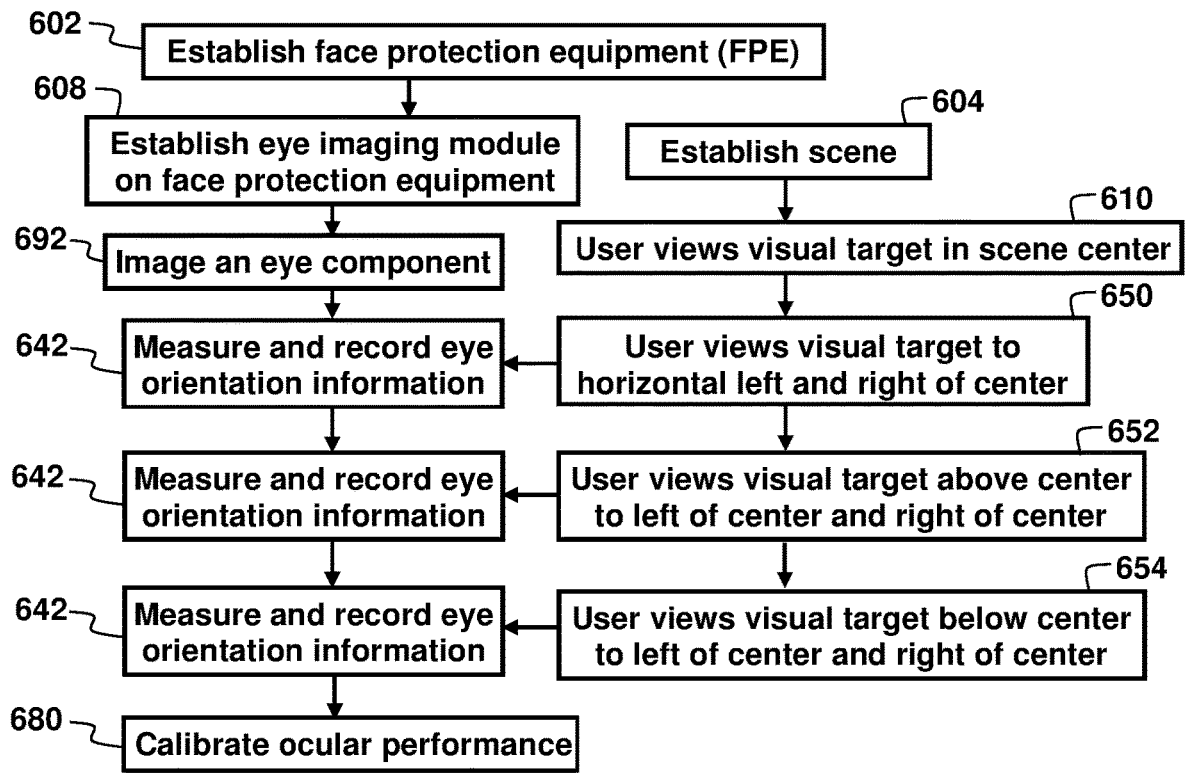
FIG. 5 shows an example of an ocular performance calibration method.

FIG. 5 shows an example of an ocular performance calibration method that can be implemented using any face protection equipment, such as the systems and devices illustrated in FIG. 2, FIG. 3, and FIG. 4. It is a specific application of the generalized method shown in FIG. 1. This method-comprises the following configuration and steps:
  1. Face protection equipment 602, that comprises an eye imaging module 608 is established. This is used to image an eye component 692.
  2. A scene is established 604. This could be a natural scene or a display of some type.
  3. The user views a visual target in the center of the scene 610.
  4. The user then views a visual target to the left and right of center 650, while eye orientation information is recorded 642.
  5. The user then views a visual target positioned superiorly (i.e., above the center of the scene) and to the left and right of center 652, while eye orientation information is recorded 642.
  6. The user then views a visual target positioned inferiorly (i.e., below the center of the scene) and to the left and right of center 654, while eye orientation information is recorded 642.
  7. This measured and recorded eye orientation information at a plurality of times 642 is then used to calibrate ocular performance 680.

In the assessments of ocular performance, described herein, it should be understood that the viewed visual target can represent a natural object or a projected target. The visual target may also be represented by normal visual targets as viewed in the field of activity or play, such as viewing the football, the helmet of another player, a piece of another player's uniform, a familiar object relative to the person's activity, or viewing a part of person's body. The ocular parameter assessment can use moving or stationary visual elements or targets and measurements can be made in a very brief period of time (e.g., seconds) to assess the human health condition or human performance.

Figure 6:
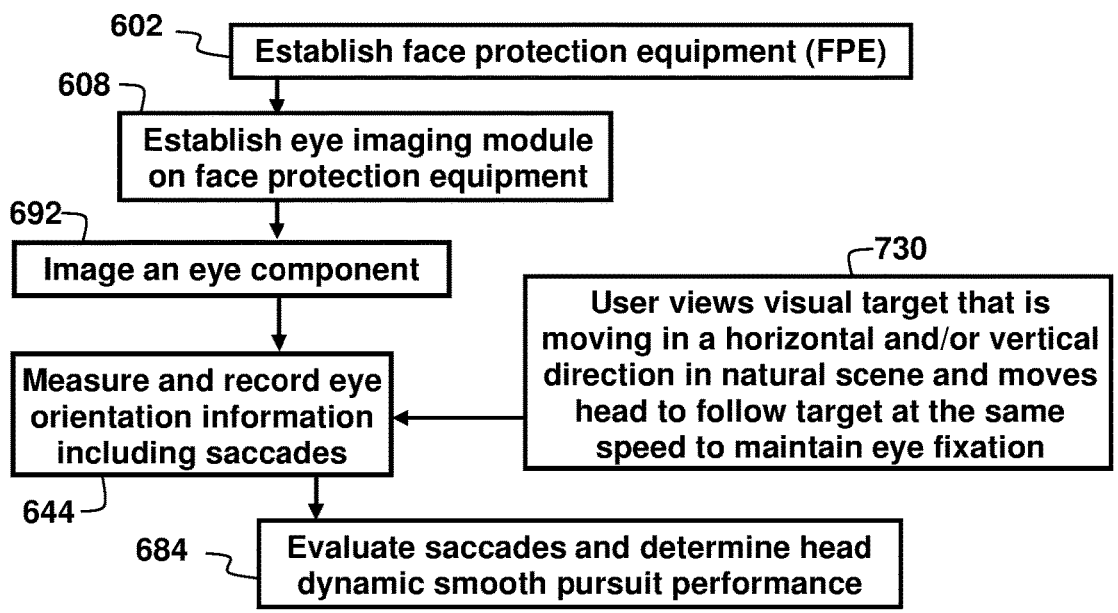
FIG. 6 shows a method for evaluating saccades and determining head dynamic smooth pursuit performance.

FIG. 6 shows an example of a head dynamic smooth pursuit performance measurement that also evaluates saccades. This example can be implemented using any face protection equipment, including but not limited to, the systems and devices illustrated in FIG. 2, FIG. 3, and FIG. 4. It is a specific application of the generalized method of FIG. 1. This method comprises the following configuration and steps:

1. Face protection equipment 602, that comprises an eye imaging module 608 is established. This is used to image an eye component 692.
2. The user views a visual target that is moving in a horizontal and/or vertical direction in a natural scene and moves their head to follow the visual target at the same speed in order to maintain eye fixation, as shown at step 730, while eye orientation information, including saccades, is measured as shown at 644.
3. This is then used to evaluate saccades and determine head dynamic smooth pursuit performance, as shown at step 684.

In one embodiment, information from measures of saccades and head dynamic smooth pursuit performance 684 could be used to determine a behavioral health condition, such as impairment with substance use.

Figure 7:
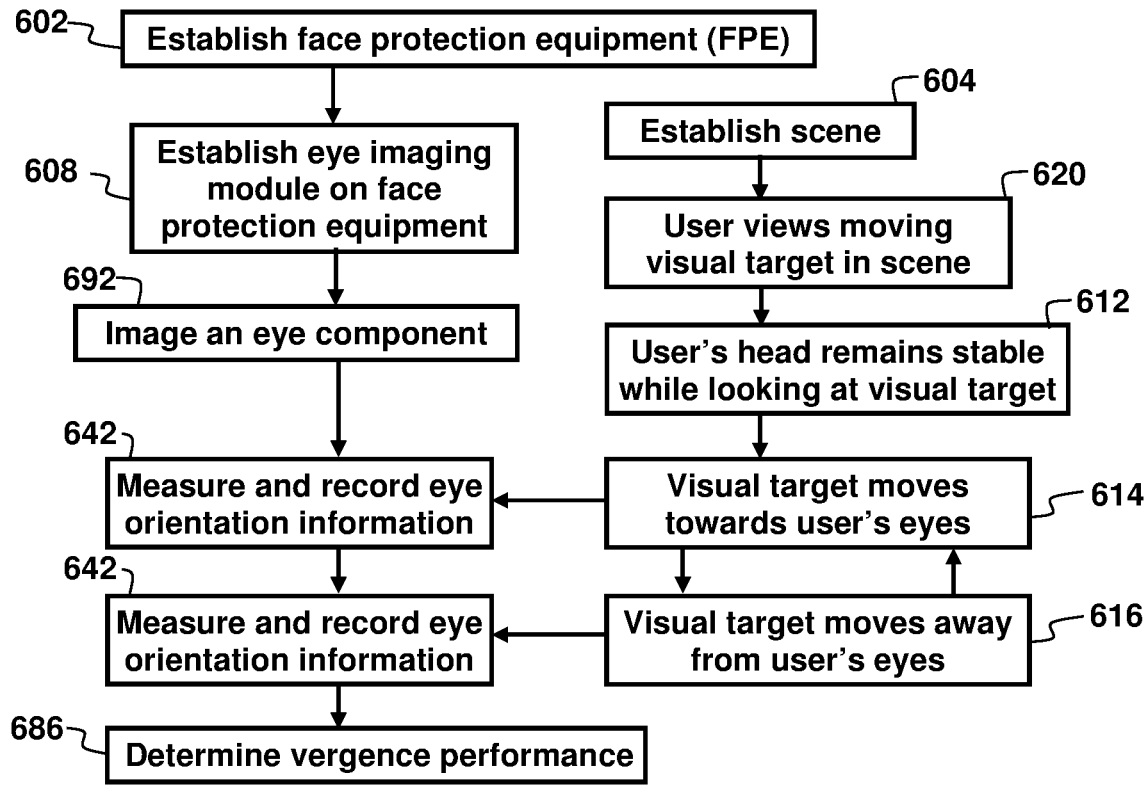
FIG. 7 shows a method for determining vergence performance.

FIG. 7 shows an example of a vergence measurement method that can be implemented using any face protection equipment as well as the systems and devices illustrated in FIG. 2, FIG. 3, and FIG. 4. It is a specific application of the generalized method shown in FIG. 1. This method comprises the following configuration and steps:

1. Face protection equipment 602, that comprises an eye imaging module 608 is established. This is used to image an eye component 692.
2. A scene is established 604. This could be a natural scene or a display of some type.
3. The user views a moving visual target in the scene 620.
4. The user keeps their head stable while looking at this visual target as shown at 612.
5. The visual target then moves towards the user's eyes 614, while eye orientation information is recorded 642.
6. The visual target then moves away from the user's eyes 616, while eye orientation information is recorded 642. This process can be repeated.
7. This measured and recorded eye orientation information at a plurality of times 642 is then used to determine vergence performance 686.

In one embodiment, information from vergence performance 686, could be used to assess neurologic health conditions, such as traumatic brain injury.

Figure 8:
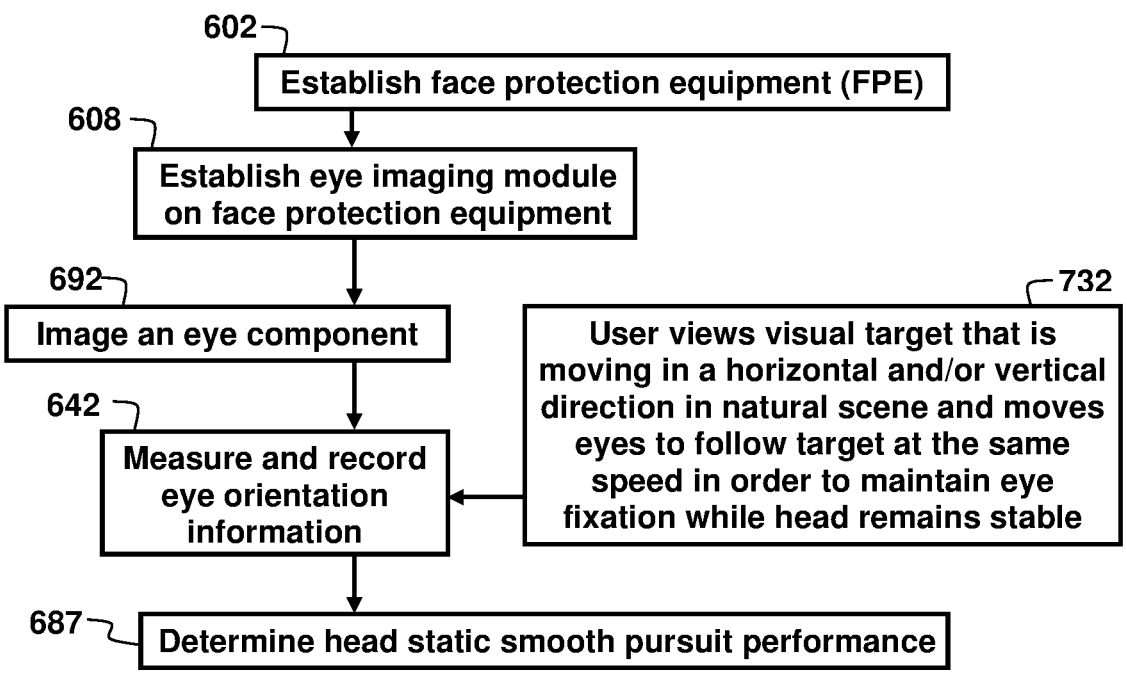
FIG. 8 shows a method for determining head static smooth pursuit performance.

FIG. 8 shows an example of a head static smooth pursuit performance measurement that can be implemented using any face protection equipment, including but not limited to the systems and devices illustrated in FIG. 2, FIG. 3, and FIG. 4. It is a specific application of the generalized method shown in FIG. 1. This method comprises the following configuration and steps:

1. Face protection equipment 602, that comprises an eye imaging module 608 is established. This is used to image an eye component 692.
2. The user views a moving visual target that is moving in a horizontal and/or vertical direction in a natural scene and moves their eyes to follow the target at the same speed to maintain eye fixation while the head remains stable, as shown at step 732, while eye orientation information is recorded 642.
3. This comparison of the movement of the visual target (from 732) and measured eye orientation (from 642) is then used to determine head static smooth pursuit performance 687.
4. Information derived from the head static smooth pursuit performance 687 can then be used for a variety of purposes, as shown at steps 800, 840, 860, 698, 820, and 821 in FIG. 1.

In one embodiment, information of head static smooth pursuit performance 687 could be used to determine mental health conditions, such as a cognitive impairment.

Figure 9:
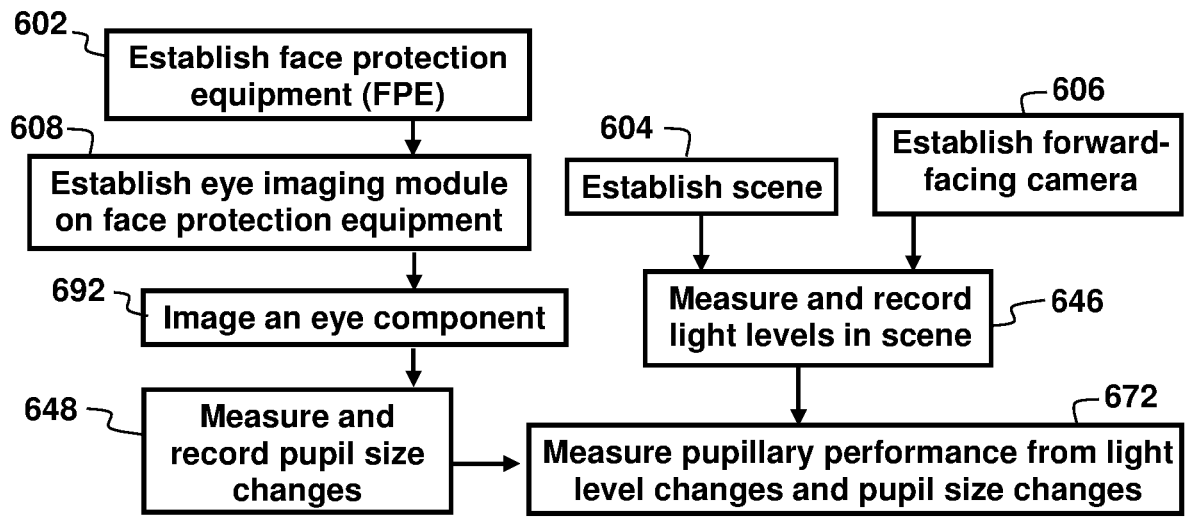
FIG. 9 shows pupil calibration and performance measurement method.

FIG. 9 shows an example of a pupil performance measurement method that can be implemented using any face protection equipment, including but not limited to the systems and devices illustrated in FIG. 2, FIG. 3, and FIG. 4. It is a specific application of the generalized method shown in FIG. 1. This method comprises the following configuration and steps:

1. Face protection equipment 602, that comprises an eye imaging module 608 is established. This is used to image an eye component 692.
2. A scene is established 604. This could be a natural scene or a display of some type.
3. A forward-facing camera is also established 606. This camera could be on the face protection equipment 602 as shown at 408 in FIG. 2, FIG. 3, and FIG. 4, or it could be separate from the face protection equipment.
4. The forward-facing camera 606 is used to measure and record light levels in the scene as shown at step 646. In this case, the forward-facing camera 606 could determine the external environment light intensity, ambient light levels, direction of light, or other dynamic changes of light and the eye imaging module 608 could measure and record the pupil size changes 648 in response to the changes in the light levels in the scene.
5. The eye imaging module 608 is used to measure and record pupil size changes as shown at step 648.
6. The light level information from step 646 is then combined with the pupil size change information from step 648 to measure pupillary performance, as shown at step 672.
7. The information from measuring pupil size changes 648 can then be used for a variety of purposes, as shown at steps 800, 840, 860, 698, 820, and 821 in FIG. 1.

In one embodiment, information from measurement of pupil size changes 672 could be used to determine a physiologic impairment 808, as seen in FIG. 1, such as with the assessed health condition of fatigue. The assessed health condition 698 could be used for control input, such as disabling a vehicle.

Figure 10:
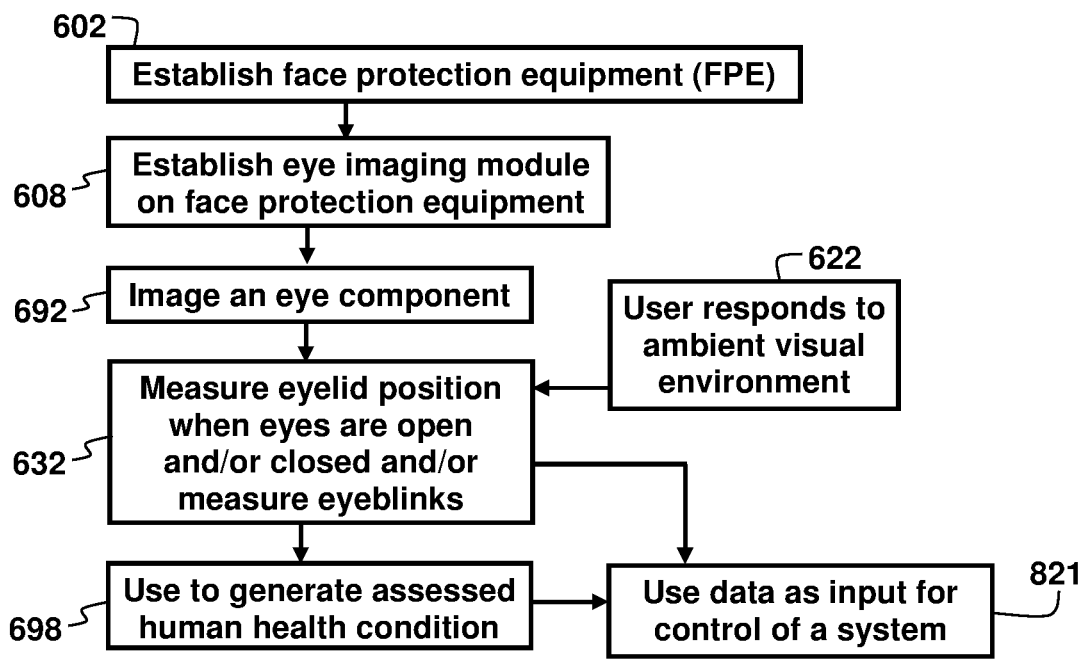
FIG. 10 shows a method for measuring eyeblinks.

FIG. 10 shows an eyeblink measurement method that can be implemented using any face protection equipment, including but not limited to the systems and devices illustrated in FIG. 2, FIG. 3, and FIG. 4. It is a specific application of the generalized method shown in FIG. 1. This method comprises the following configuration and steps:

1. Face protection equipment 602, that comprises an eye imaging module 608 is established. This is used to image an eye component 692.
2. For this measurement the eye component that is measured is the eyelid and the measurement at step 632 is information, such as (a) when the eyes are open and or closed, and/or eyeblinks.
3. The eyelid measurements from 632 can then be converted to eyeblink measures in step 632. Examples of eyeblink measures can include eyeblink duration, interblink interval, blink rate (frequency), amplitude, velocity, latency, asymmetry between the eyes and completeness.
4. This eyeblink measurement 632 can then be used for a variety of purposes, as shown at steps 800, 840, 860, 698, 820, and 821 in FIG. 1.
5. In one embodiment, information from measurement of eyeblinks 632 could be used to determine a behavioral health condition impairment 805, as seen in FIG. 1, such as with the assessed health condition of substance use impairment. The assessed health condition 698 could be used for control input 821, such as disabling a vehicle.

In an alternative embodiment of FIG. 10, the face protection equipment described in this document, may not be worn and an example of this can be a motorcycle windshield, automobile windshield, boat windshield, or aircraft windshield. In this instance, FIG. 10 can illustrate an example of how the measurement of eyeblinks at step 632, could be used as input to the control of a system 821, such as controlling a vehicle.

Figure 11:
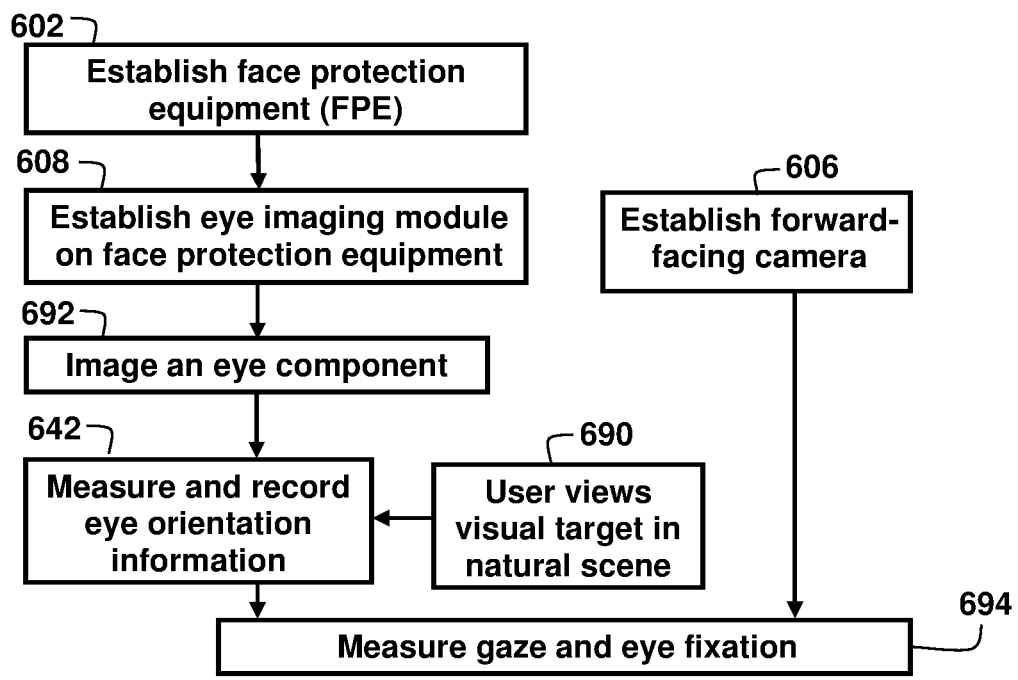
FIG. 11 shows a method for measuring gaze and eye fixation.

FIG. 11 shows an example of an assessment method that uses face protection equipment as described in this document for gaze and eye fixation measurement. This method uses face protection equipment 602 that comprises an eye imaging module 608, to image an eye component 692. In this example, the user views a natural scene while performing normal activities. Eye orientation information is recorded in step 642 and is used to measure gaze and eye fixation as shown in step 694. Here is another way to describe key elements of the gaze and eye fixation assessment system shown in FIG. 11:

1. Face protection equipment 602, that comprises an eye imaging module 608 is established. This is used to image an eye component 692.
2. The eye imaging module 608 measures eye movement and/or eye position and/or eye orientation 642.
3. The user views a visual target in a natural scene 690 and this visual input is processed in the subject's visual cortex.
4. The subject's oculomotor system activates extraocular muscles. The planned eye movement is executed through the activation of the extraocular muscles, leading to a shift in gaze.
5. Extraocular muscles shift eyes to gaze the area of interest toward a specific point of interest and can encompass various movements.
6. The eye imaging module images an eye component 692 to measure and record eye position, eye movement, and or eye orientation (step 642) while the user is viewing the visual target in the natural scene as was described for step 690.
7. The eye movement brings the gaze to a specific point in the visual scene, and the eyes stabilize to maintain eye fixation on that point.
8. A processor in the system uses the recorded eye orientation information 642 to measure gaze (where a person is looking) and eye fixation (ability to continue to look at this same visual target) 694.
9. The ocular parameter information (in this case eye fixation performance) is a specific example of measured ocular parameters (step 693 in FIG. 1) that can then be compared to baseline values (step 800 in FIG. 1) to complete the other steps in FIG. 1, in FIG. 12, in FIG. 13, or in FIG. 14.

Note that gaze and eye fixation can be measured by using infrared (IR) light to illuminate the eyes. Infrared light reflects off the cornea creating a glint on the eye's surface, which can determine the direction of gaze. The IR light could come from a source attached or embedded in the eye imaging module, or the IR source could be separate from the eye imaging module. Micro-opto-electro-mechanical systems (MOEMS) sensors can be used to direct and control IR light emission. The captured images can then be processed to extract information about the position of the pupils, corneal reflections, or other features indicative of gaze direction. Alternatively, video cameras could capture images or video of the user's eyes and these video cameras could include multiple sensors for better accuracy. Sensors can monitor changes of eye position to measure gaze and eye fixation.

Note that the natural scene 690 must either have a visual target in a known location, or there must be some device to view and identify the location of the visual target. A forward-facing camera 606 (shown at 408 in FIG. 2, FIG. 3 and FIG. 4) could be used to determine the location of the visual target in order to measure gaze and eye fixation 694. The forward-facing camera 606 can be configured to capture images or video of the user's surroundings (as shown at 432 in FIG. 2), and computer vision algorithms can identify and locate objects (as shown at 434 in FIG. 2) within the scene. The forward-facing camera can provide information about the location of the target that can then be compared to the user's gaze direction. The user's gaze direction is determined by the eye imaging module 608 that images an eye component 692 to measure and record eye orientation information 642. By combining information from both sources (e.g., eye imaging module 608 and forward-facing camera 606) the user's gaze and eye fixation performance can be determined. Machine learning models can be trained to associate patterns in the visual scene with specific visual targets.

Figure 12:
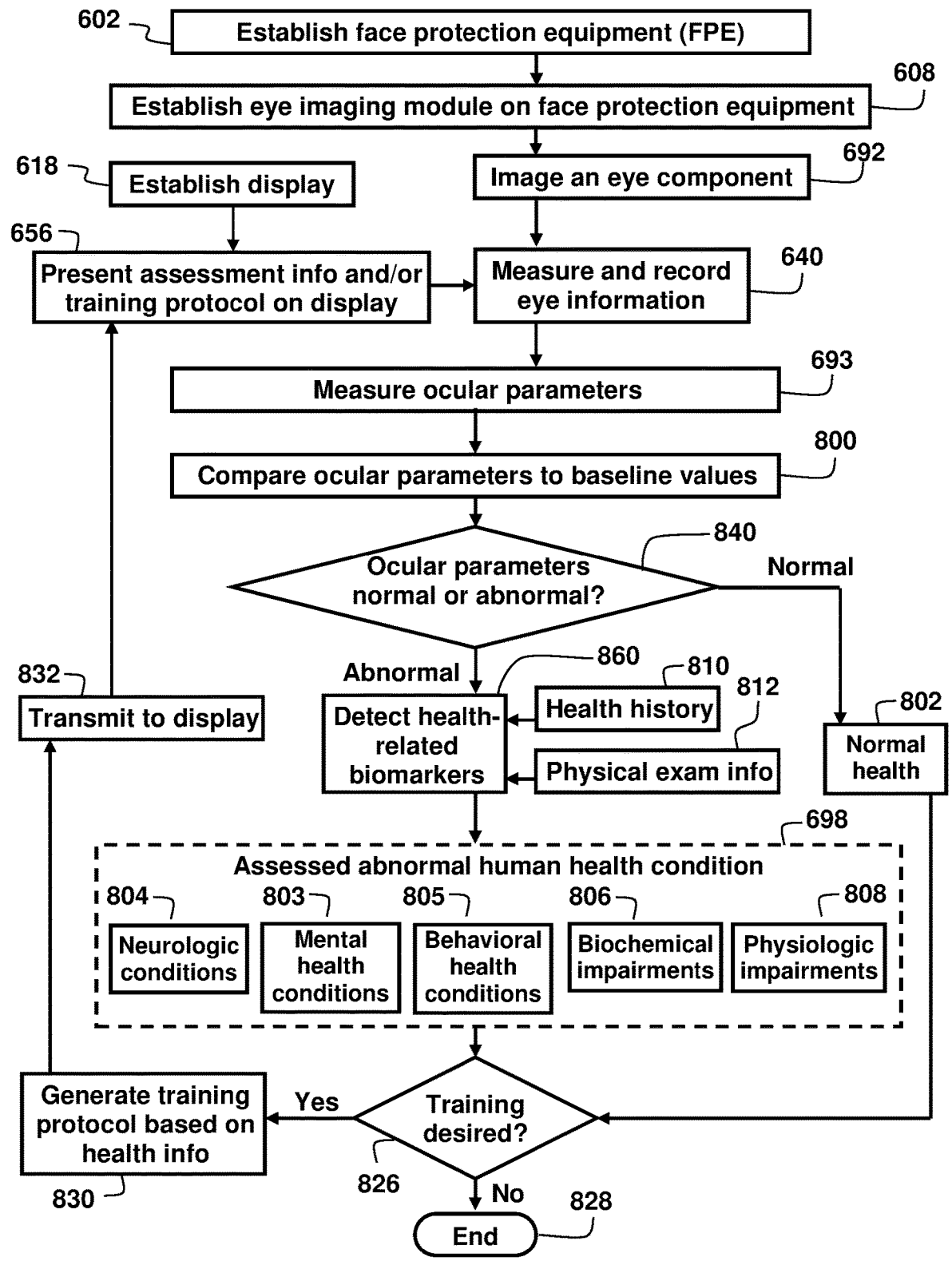
FIG. 12 shows a training, rehabilitation, and/or performance enhancement method.

FIG. 12 shows an example of an assessment method that uses face protection equipment (FPE) to assess a health condition and use this information for training. This training could be for health condition improvement (step 820 in FIG. 1) or for supernormal performance (step 822 in FIG. 1). The assessment and training process comprises the following configuration and steps:

1. Face protection equipment 602, that comprises an eye imaging module 608 is established. This is used to image an eye component 692.
2. A display is established 618. The display could be part of the face protection equipment or an external display, such as the display shown at 432 in FIG. 2.
3. The display 618 is used to present assessment information and or training protocols, as shown at step 656.
4. Eye information is measured and recorded, as shown at 640. This could be any of the types of eye information described in this document.
5. This measured eye information from step 640 can be used to measure any of the ocular parameters that have been discussed herein, as shown at step 693.

6. These ocular parameters 693 could be compared to baseline values 800 to determine if these ocular parameters are abnormal, as shown at step 840.
7. If ocular parameters indicate normal health 802, the process can move directly to a decision box to determine if training is desired 826. If training is desired, this training would be used to develop supernormal capabilities, as was shown at 822 in FIG. 1.
8. If ocular parameters are abnormal (from 840), these parameters could be combined with health history 810 and physical exam info (812) to detect health related biomarkers, as shown at step 860.
9. These biomarkers from step 860 could then be used to assess a human health condition 698, which could be a neurologic condition 804, a mental health condition 803, a behavioral health condition 805, a biochemical impairment 806, or a physiologic impairment, as described in other parts of this document.
10. If the ocular parameters from 698 indicate an abnormal condition, the process can move to the same decision box described previously for normal health, shown at 826. In this case, if training is desired, this training would be for health condition improvement, as shown at step 820 in FIG. 1.
11. If training is not desired at step 626, the process ends at step 828.
12. If training is desired, a protocol can be generated at step 830, and this protocol can be based on the health information from 698.
13. The training protocol from 830 can be transmitted to the display 832 and presented on the display, as shown at 656, allowing the cycle to be repeated.

Further referring to FIG. 12, the human subject's health condition 698 could be enhanced to a "supernormal" level with visual training, and/or this health condition from 698 could be treated with visual-oculomotor (VO) rehabilitation if an abnormality of any ocular parameter is detected. Visual training with repeat ocular parameter methods, can provide an above normal level of eye fixation for performing athletic or occupational activities. While VO rehabilitation is often referred to as restoration of a visual acuity impairment, in this document and embodiments it also refers to performing specific visual rehabilitation tasks required to restore ocular parameters to normal, which were found to be previously abnormal. If an abnormality is detected with one or more of the specific ocular parameters being tested, a specialized program can be viewed. For example, if an abnormal VO impairment is detected with a TBI (traumatic brain injury) or other impairment, the individual can receive a VO rehab program, like the method shown in FIG. 1, but in repetitive fashion, in different directions and with optimizing the visual elements to enhance visual fixation. Effective rehabilitation interventions initiated early after a traumatic brain injury has been shown to enhance the recovery process and minimize the functional disability. The return of normal ocular parameters can provide a precise risk assessment to guide the determination for return to play activities with high performance predictability, based on the ability for return of measured eye movement responses to achieve normal values.

With reference to step 830 in FIG. 12, the training protocol (or training information) is responsive to the ocular parameter measurement from step 693, compared to baseline values (normal values) from step 800, which allow the detection of one or more abnormal ocular parameter(s) 840. The abnormal ocular parameter 840, in combination with the health history 810 and physical exam information 812 can establish the health-related biomarkers 860, which in turn allow the assessment of health status 698. With the knowledge of knowing the health condition 698, it can be determined if rehabilitative training 826 is necessary, enhancement of visual-oculomotor training is desired, or no training is needed or desired. If training is desired, a protocol based on health condition 698 information can be generated at step 830. The following table illustrates more specifically how the abnormal ocular parameters from step 840 can be used to generate the training protocols. This table gives an example of the behavior of the visual target and instructions for the individual to follow.

| Abnormal Ocular Parameter | Generated training protocol |
| --- | --- |
| Abnormal saccades | Eye fixation stabilization training, which can be combined with balance training to reduce saccadic activity and improve saccade accuracy:<br>a. Visual target is focused upon to reduce microsaccades.<br>b. Individual views visual target, ensuring that head is aligned with target, then views target to left, then right. This can be repeated at different speeds.<br>c. Individual view visual target, ensuring that head is aligned with target, then views target above, then below. This can be repeated at different speeds.<br>d. Balance training tasks, such as standing, or walking can be added while the subject repeats the above tests. |
| Abnormal vergence | Eye fixation stabilization training exercises, which can be combined with balance training:<br>a. Individual views a visual target as the target is moved toward the nose.<br>b. The target continues to move toward the nose until double vision occurs. At this point, the target is moved away until the double vision resolves. The distance of the visual target moving away from the nose can vary.<br>c. The target is held stationary for a few seconds while the subject focuses on the visual target and the training exercise is repeated.<br>d. Individual can work on improving this threshold by achieving a closer distance from the nose each time.<br>e. Balance training tasks can be added, such as doing the above exercise while standing with feet together, split stance (one foot in front of the other), or on one foot. |

| Abnormal Ocular Parameter | Generated training protocol |
|---|---|
| Abnormal head static smooth pursuit | Eye fixation stabilization training exercises, which can be combined with balance training:<br>a. Individual views a visual target as the target is in motion, with head remaining stable.<br>b. The target in this exercise can move in any direction and at different speeds.<br>c. Individual then focuses on two separate targets, alternating between them in the horizontal plane and/or the vertical plane.<br>d. Individual uses quick eye movements to move the visual focus from target to target in a zig-zag pattern.<br>e. Individual can also focus on visual target motion of a bouncing ball or other visual target object. |
| Abnormal head dynamic smooth pursuit | Eye fixation stabilization training exercises:<br>a. Individual focuses on a stationary object while moving the head slowly side to side, up and down, or in circular motions.<br>b. Individual moves the head while maintaining focus on a target. This includes moving the head while following a moving object with the eyes. |
| Abnormal dynamic visual acuity | Eye fixation stabilization training:<br>a. Individual maintains visual fixation on an enhance visual target while moving head horizontally and vertically.<br>b. Individual reads letters written on moving visual targets.<br>c. Individual reads smallest letter displayed while head is in motion. |
| Abnormal pupil performance | Pupil control is balanced between sympathetic and parasympathetic nervous system:<br>a. Individual alternates between rest and relaxation of eyes.<br>b. Avoid direct light in eyes.<br>c. Gradual exposure to varying light conditions with biofeedback. |
| Abnormal eyeblinks | a. Individual practices conscious and controlled training of firm blinks<br>b. Practice blink rate and alter incomplete blinks. |

Further referring to the table above, it should be noted that dynamic activity (walking or other movement) could be added to any of the above training protocols. Such requested movements could be performed at a prescribed metronomic pace. The above training protocols could be performed by the individual multiple times per day. Additionally, visual targets viewed could be enhanced to provide improved eye fixation ability and minimize saccade activity.

Figure 13:
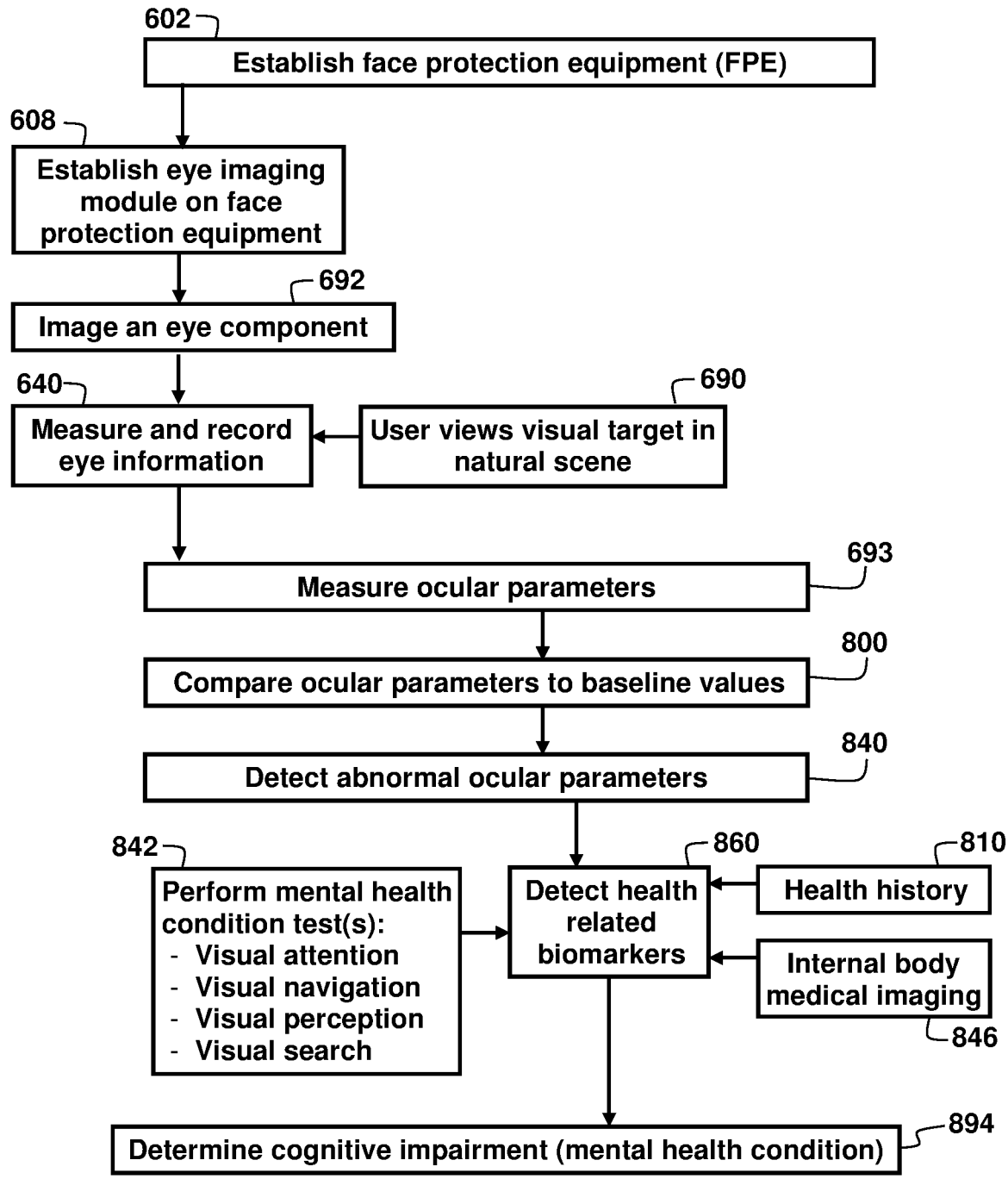
FIG. 13 shows a method for assessing mental health conditions.

FIG. 13 shows an example of a method for using face protection equipment, as described in this document, to detect cognitive impairment, a type of mental health condition described in this document. This assessment comprises the following configuration and steps:
1. Face protection equipment 602, that comprises an eye imaging module 608 is established. This is used to image an eye component 692.
2. While a user views a natural scene 690, eye information is measured and recorded, as shown at 640.
3. This measured eye information from step 640 can be used to measure any of the ocular parameters that have been discussed herein, as shown at step 693.
4. These ocular parameters 693 could be compared to baseline values 800 to detect abnormal ocular parameters 840.
5. The abnormal ocular parameters 840 could be combined with internal body medical imaging 846 (such as CT scans, MRI, ultrasound, etc.), the results of mental health function tests 842, and health history information 810 to detect health related biomarkers, as shown at step 860.
6. The biomarkers 860 could then be used to assess a human health condition, which in this case is a cognitive impairment, a type of mental health condition, as shown at 894.

Regarding step 842 in FIG. 13, there can be numerous visual mental health function tests. Examples include:
(a) Visual attention assessment can be achieved by measuring the duration of sustained attention of an individual's eye fixation on a specific visual target over time.
(b) Visual navigation can be measured by quickly identifying a visual target of interest, and the individual's ability to execute smooth pursuit of eyes while following the target along different paths, and quickly identifying visual targets. The reaction time, accuracy, and errors are also recorded.
(c) Visual perception can be measured by an individual's ability to focus on a selected visual target and screen out or ignore irrelevant objects, and associations between the objects.
(d) Visual search can be measured by an individual's ability to locate and identify a specific visual target within a scene, which may be complex with other objects. The visual target of interest could be an object related to the activity the individual is engaged in and the scene can be comprised of visual stimuli of varying complexity. The reaction time, accuracy, and errors can then be recorded.

Figure 14:
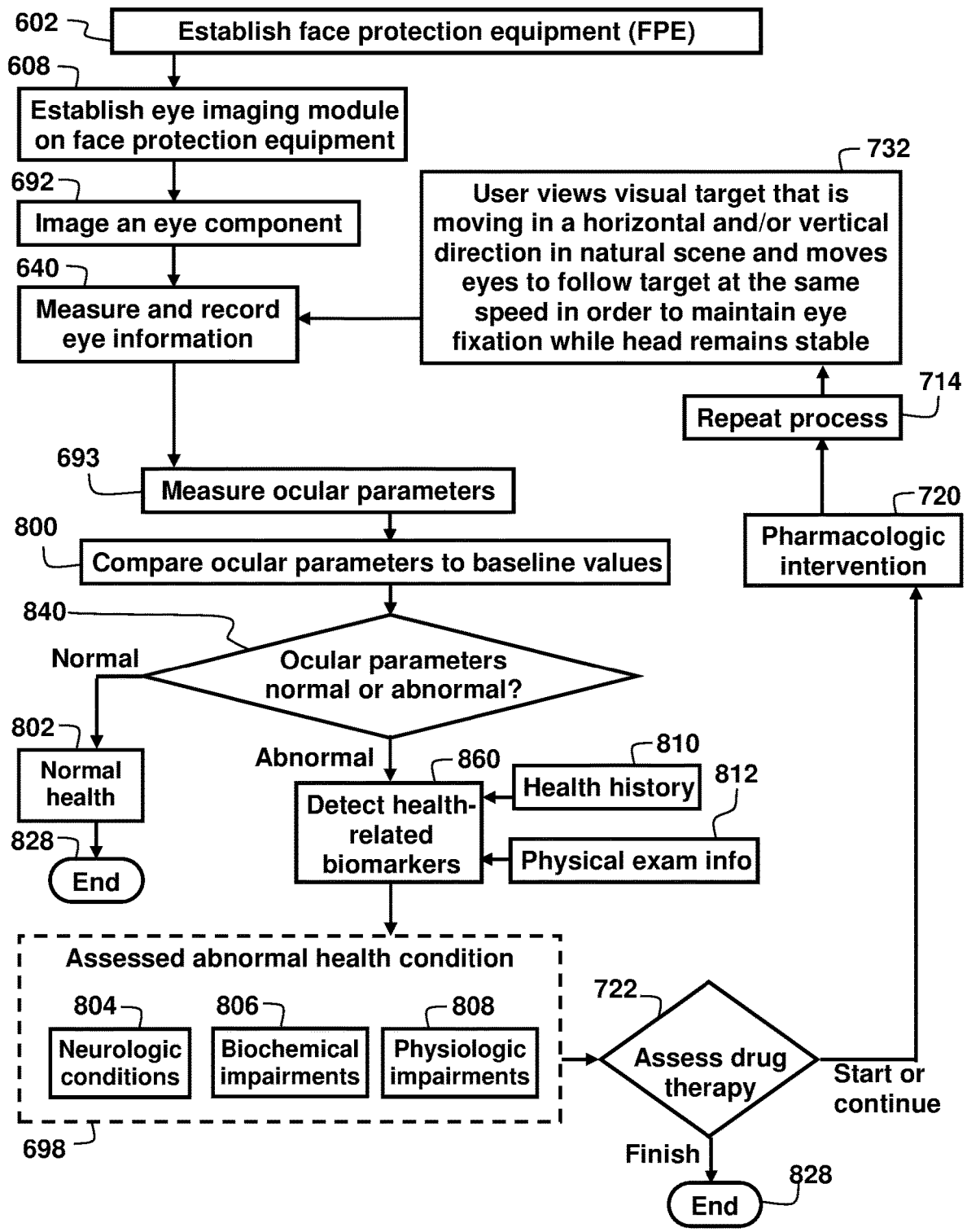
FIG. 14 shows a system for pharmacologic intervention and assessment.

FIG. 14 shows an example of an assessment method using the face protection equipment to categorize health condition differences and determine pharmacological intervention effects on measures of ocular parameters for individuals having neurologic conditions, biochemical impairments, and/or physiologic impairments.

This method comprises the following configuration and steps:
1. Face protection equipment 602, that comprises an eye imaging module 608 is established. This is used to image an eye component 692.

2. The user views a visual target that is moving in a horizontal and/or vertical direction in a natural scene and moves eyes to follow target at the same speed in order to maintain eye fixation while the head remains stable, as shown at step 732. Eye information is measured and recorded while this is going on, as shown at step 640.
3. The eye information from step 640 is then combined with information about the natural scene from 732, to measure ocular parameters, as shown at step 693.
4. These ocular parameters 693 could be compared to baseline values 800 to detect if the ocular parameters 840 are abnormal.
5. If the ocular parameters from step 840 indicate normal health 802, the process ends, as shown at 828.
6. If the ocular parameters from step 840 are abnormal, this information can be combined with physical exam information 812 and health history information 810 to detect health related biomarkers, as shown at step 860.
7. The biomarkers 860 could then be used to assess a human health condition 698. In this case, a neurologic condition 804, biochemical impairment 806, or physiologic impairment 808, could be identified.
14. As shown at decision 722, if health is normal, the process ends 828. If health is not normal, a pharmacologic intervention could be made, as shown at step 720, and the process described above could be repeated.
15. If pharmacologic intervention 720 is used for an abnormal health condition 698, then the process of measuring the ocular parameters 693 can be repeated at step 714 to determine if the ocular parameters are still abnormal or normal 840. If there are no further abnormal ocular parameters, it would indicate normal health 802 and the process ends at 828. If an abnormal ocular parameter persists with the related health biomarker 860, further assessment 722 can be made about terminating the drug and ending the process 828 or continuing with pharmacologic intervention 720. This could be with the same drug or different drug therapy and the process can be repeated 714 as often as necessary to assess pharmacologic intervention with measurement of ocular parameters 693 to determine the status of the health condition as necessary.

Further referring to FIG. 14, in one embodiment if a neurologic condition is determined to be abnormal and pharmacological therapy is determined to be necessary or indicated, the technology described herein can be used to assess efficacy of administered drug therapy. The assessed abnormal health condition could even be obtained from accumulation of stored health-related biomarker data over time in the cloud, which when detected for an abnormality, using artificial intelligence, could automatically generate an electronic pharmacological prescription. This therapeutic intervention could then be more objectively assessed.

There can be numerous other embodiments, capable of being understood by anyone skilled in the art, using the above-described figures which use eye sensors for measurement of ocular parameter to assess the human health condition, including neurologic conditions, such has traumatic brain injury, mental health conditions, such as depression, behavioral health conditions, such as substance use impairments, biochemical health impairments, such as metabolic dysfunction, and/or physiologic health impairments, such as fatigue.

FURTHER EMBODIMENTS

In this document and other embodiments, the system for assessing a human health condition discussed herein can be comprised of artificial intelligence (AI) or train a machine learning-based model used for detecting the eyelid position based on the eye surface characteristic reflections, extracting eyelid positions by analyzing the images (image-based positions), generating data points based on the image-based positions; generating digital values based on the reflections; and providing the data points and digital values to train the machine learning based model for detecting the eyelid position based on the eye surface reflections. Quantum computing can also be used for processing and analyzing visual information. Quantum algorithms could be used to enhance image recognition and processing tasks relevant to eye tracking applications. Quantum machine learning algorithms could be applied to eye-tracking data for improved pattern recognition and analysis, helping in areas such as gaze prediction and understanding visual attention.

In another embodiment, the discussed system above can also comprise a forward-facing camera, configured to transmit video information, and which can communicate with the electronic circuit, and eye imaging sensors. This can be used to determine location of gaze, identify and correct slippage offsets of the face protection equipment.

In another embodiment, the forward-facing camera with light sensor can calculate the ambient light level and then adjust the amount of light (e.g., brightness or dimness) entering the eye, which can be used for a measurement of ocular parameters, such as pupil size.

In another embodiment, the system described can be comprised of physiologic and biochemical sensors, which are in contact with the skin to provide biochemical and physiologic information from the body, which can communicate with the electronic circuit, eye sensors, body sensors and the recorded data from the physiologic and biochemical sensors can be correlated with the ocular parameter measures.

In an embodiment, the present invention can be comprised of face protection equipment which uses eye and head rotation information to measure ocular parameters to assess human health. The eye information can be acquired from an eye sensor that is comprised of at least one opto-electric transducer configured for converting a light signal to an electrical signal and information can be acquired from the head rotation sensor. The head rotation sensor and eye imaging sensor(s) can be integrated into the face protection equipment. The system described is configured for measuring the position and movement responses of the eyes and head.

In the embodiments discussed herein, features include a forward-facing camera, eye imaging device, head rotation sensor controlled by an electronic circuit. Components of the electronic circuit can be activated or controlled haptically, auditorily, remotely, wirelessly, with gestures or movement of the eyes, head, hands or manually with a power switch on the device. Additionally, a bone or air conducting sensor can be incorporated in the framework of the device which can provide auditory/acoustic signals to issue an input signal to a controller to operate the system. The electronic circuit can also be activated by placing the face protection equipment on the head which can issue a similar input signal when in contact with the skin and when removed from the head, the system will automatically become deactivated.

In an embodiment of the device, the system may include the user interface for providing information to the user of the device. The user interface may be associated with a touchpad, a keypad, buttons, a microphone, a haptic device, and/or other peripheral input devices. The processor may control functions of the system based on input received through the user interface. The system and/or testing function controls and input connections can be in the face protection equipment and/or in a remote device. The computing system could be a distributed computing system. The computing system could comprise cloud computing. The ocular parameter measure methods can be comprised of an application connected to a cloud-based artificial intelligence infrastructure. The application can be made up of a series of tasks, and a user's eye movement can be recorded in data sets called Eye Movement Biomarkers (EMBs) and Gaze Mapping.

In one embodiment, the face protection equipment or method can present a visual target to one eye (monocular) or both eyes (binocular). A power source can be attached to the FPE, and which can be rechargeable by a wireless interface.

In another embodiment, the face protection equipment described herein can measure information between position and orientation of the head and eye position, and/or movement and/or eye reflexes and the ocular parameter being assessed. The data acquired can be processed by the face protection equipment and displayed to the user or collected data can be transmitted wirelessly to a smart phone, electronic device, or other computer source for the processing and viewing.

In an embodiment, the face protection equipment can include an eye imaging and measuring system, a connected head rotation and measuring system, a power supply, a micro-processor, a memory, and a user interface. Components of the system may be configured to work in an interconnected fashion with each other and/or with other components coupled to respective systems. For example, the power supply may provide power to all the components of the system. The processor may receive information from all the affixed sensors and control the eye imaging system and the body rotation or orientation system.

In another embodiment, face protection equipment can have a manual control operating switch with an active and inactive mode. It can be comprised of an imaging device, a head rotation sensor, physiologic sensors, biochemical sensors, and an electronic circuit comprising a central processing unit with memory unit. Collected data can be transmitted to a small electronic device where easily understandable results can be seen.

In another embodiment, a mental health condition can be assessed by an abnormal ocular parameter and/or an abnormal mental health function assessment from a group of cognitive assessment tools including attention, navigation, perception, and search assessments.

In an embodiment, cognitive training and/or cognitive feedback can be performed and measured by comparing the eye position and/or movement between each eye, between the position and/or movement of the eyes and between the position and/or movement of a natural scene target and eyes.

In embodiments of the invention, the imaging device can comprise components configured to provide images of eye position and eye movement using components of the eye. The components can include a light source, diffracting elements to alter the light source, and opto-electric transducer configured for converting the light signal to an electrical signal. Both imaging device and head rotation sensor components can be electrically coupled such that eye information can be compared to head rotation signals with ocular parameter measurements.

In an embodiment, ocular parameter measurements can provide an indicator of the response to a pharmacologic therapeutic intervention.

In another embodiment, ocular parameter measurements can provide a neurologic, or physiologic indicator of a response to a therapeutic intervention.

In another embodiment, saccadometry and specifically prosaccade and antisaccade measures can be used to detect behavioral health conditions, mental health conditions, and neurologic conditions.

In an embodiment, vergence can be measured and compared in both eyes, as the visual target in the subject's visual field appears to move forward and away from the individual's eyes. This movement of the visual target can be a continuous transition, or it can occur in a series of distinct stages. Poor vergence performance can be recorded, indicating abnormal changes of accuracy, convergence, divergence, peak velocity, amplitude, symmetry, or latency, and can be used to determine neurologic conditions, such as TBI, biochemical impairments such as metabolic dysfunction, as well as physiologic impairments such as fatigue or intracranial fluid pressure impairment.

In another embodiment, vergence can be measured during continuous transition of different depths vertically, horizontally, or diagonally as the visual target gets closer or further from the user's eyes combined with dynamic motion of the head, which is moving in the same pattern or direction as the visual target.

In another embodiment, assessment of vergence dysfunction is performed for detection and/or quantification of acute traumatic brain injury, and/or recovery and is comprised of disconjugate movement of the eyes to track objects varying in depth over the visual field.

In another embodiment, saccades can also be measured using the face protection equipment as discussed in this document, during other ocular parameter measures including vergence, head static smooth pursuit, and head dynamic smooth pursuit. The occurrence of saccades, saccadic intrusions, or saccade dynamics on fixational eye movement during ocular parameter measure can be related to neurologic conditions or impairments of human health.

In another embodiment, head static smooth pursuit can be measured while the head remains stable, and the eyes are focused on a visual target which is moving in various directions. An abnormal head static smooth pursuit performance can be indicated by abnormally measured eye movement and/or eye position and/or eye orientation changes of gain (peak velocity/target velocity), velocity changes, accuracy of following a moving object or latency. These abnormalities can assess neurologic conditions like TBI, physiologic impairments such as fatigue and biochemical impairments due to hormone or electrolyte abnormalities.

In an embodiment, pupil performance can be measured by determining pupil size at least on one side, and features of the pupil, while viewing stationary alternating bright and dim targets seen in the visual field. Alternatively in another embodiment, these visual targets, having varied light intensities, can be moving toward or away from the eye, or they can be presented in different positions with different characteristics, requiring the subject to recognize the difference between the visual targets. Poor pupil performance can include abnormal measures of pupil size, dilation information of acceleration, amplitude, latency or duration, and constriction information of amplitude, latency, or duration. These abnormal pupil measures can detect neurologic conditions like concussions, biochemical impairments with metabolic dysfunction, and physiologic impairment with cardiac disease, such as hypotension.

In an embodiment, eyelid performance can be measured and compared between each eye with a visual stimulus, at various intensities of brightness, with varied task content and at varying speeds causing eyeblinks. Abnormal eyelid performance can be associated with abnormal velocity of eyeblinks, duration of eyeblinks, amplitude or frequency of eyeblinks which can detect the presence of neurologic conditions, such as concussions, biochemical impairments associated with electrolyte or metabolic dysfunction and physiologic impairments which occurs with fatigue, or lack of alertness.

In another embodiment, a concussion can be detected by viewing a visual stimulus and capturing eyeblink raw data from at least of one eye of the subject in response to the visual stimulus, using an eye imaging device and analyzing eyeblink frequency.

In an embodiment, a concussion can be detected by viewing a visual stimulus and capturing eyeblink raw data from both eyes of the subject in response to the visual stimulus using an eye imaging device and analyzing the number of blinks in one eye of the subject that does not have a corresponding blink frequency rate in the other eye of the subject.

In another embodiment, anyone of the ocular parameter measurements discussed in this document can be used to assess the condition of human health and implemented for training athletes or other individuals in their occupational activities, to assume a supernormal level of performance.

In another embodiment, the face protection equipment as described in this document, comprised of an eye imaging device, and electronic circuit can be configured for use with machine learning such that a classifier can recognize any abnormal ocular parameter measured and provide classification of raw gaze datasets, belonging to eye fixations, saccades, or other predetermined categories. The classified algorithm or quantum algorithm can be used to assess whether the data can be used for training or specific visual rehabilitation, based on the abnormal datasets, and can modify an attribute of the training or visual rehabilitation according to the measured ocular parameters.

In an embodiment, the face protection system discussed herein can be portable, autonomous, constantly sensing head and eye information with the use of an artificial intelligence (AI) program, or quantum algorithms, and/or classifiers to assess the human health condition and can provide this information to the user as well as wirelessly transmit this information to a remote electronic device.

In an alternative embodiment, the present invention can visually rehabilitate or retrain the user when a specific ocular parameter abnormality is present. Visual-oculomotor-vestibular (VOV) rehabilitation can enhance ocular parameter visual accuracy with specific visual stimulation and body movements. VOV rehabilitation can help a user of the device improve the health conditions or impairments by exercising, enhancing, and/or retraining the abnormally detected ocular parameter. This type of rehabilitation system can also provide more rapid recovery of an abnormal ocular parameter by visually stimulating the associated neurologic pathway and connections affected by the neurologic, physiologic, or biochemical impairments with repetitive ocular parameter techniques.

In another embodiment, ocular parameter assessment can be used to train the oculomotor system and brain with individualized program, which can increase accuracy of eye fixation, cognition, attention, reaction time, fatigue, and treat traumatic brain injuries and mental health impairments.

In an embodiment, mental health assessment and/or training can be performed with an eye imaging device which measures the right and left eye movement, and/or eye gaze positions, and/or eye orientation during the time a viewed object is moving on a display and measured. Disconjugate measurement between the eyes is compared to detect an oculomotor impairment. A report can be provided if a disconjugate measure is present, indicating the presence of an oculomotor impairment and/or mental health condition. Disconjugate measures can also be used for training to improve a mental health condition or oculomotor impairment.

Alternatively, in another embodiment, mental health assessment or behavioral health assessment can be performed with an eye imaging device to measure eye movement, and/or eye gaze position, and/or eye orientation. A measured analysis can be generated from the eye measurement information (e.g., eye movement. and/or eye gaze position, and/or eye orientation) of at least one eye can be compared to the position of the object observed by the user. Another measured analysis, representing a physiologic impairment and/or mental health condition analysis can be generated when there is a difference between eye measurement information and the position of the object viewed by the user.

In another embodiment, ocular parameter measurement can be used for assessment, management, and rehabilitation periodically to analyze the progress of mental health conditions. A mental health rehabilitative program can be used to improve specific cognitive impairments. Mental health testing can also be used for assessing deployment or occupational activity readiness, situational awareness, predicting human performance, and stress management.

In another embodiment, an artificial intelligence health platform can be operable for autonomous operation using a variety of learning methods and/or predictive analytic techniques to assess the health conditions and/or need for rehabilitation and/or training. The artificial intelligence health platform, comprised of a plurality of different engines can assess neurologic conditions, mental health conditions, behavioral health conditions, physiologic impairments, biochemical impairments and determine human performance capability.

In another embodiment, artificial intelligence (AI) and machine learning can be used analyze the results of ocular parameter assessments, in tandem with visual mental health function assessments discussed herein, patient records and reported symptoms, to diagnose the type and severity of mental health conditions.

In an embodiment, the information collected from ocular parameter measurement(s) of a user can be logged, stored, and transmitted to another data collection source.

In another embodiment, the collected eye and head movement data from ocular parameter measurements can use artificial intelligence and machine learning to detect health-related biomarkers related to detecting and diagnosing health conditions, such as CTE, with abnormalities of mental health function and behavior to automatically personalize VOV rehabilitation therapy plans. This VOV rehabilitation therapy can also access the software therapy from the cloud, through a smartphone, or other electronic device. Once the measured ocular parameters assess the health condition of the subject, the identity proofing, privacy, and security for the subject can be established. Information regarding normal ocular parameters and/or abnormal ocular parameters can be wirelessly transmitted to the cloud. Artificial intelligence and machine learning in the cloud can establish the rehabilitation program needed, based on the abnormal ocular parameter measured, or further training desired by the subject to obtain above normal performance with the selected parameter.

In another embodiment, the specific electronic prescription, determined by the computer code (machine learning algorithm) in the cloud or other external electronic device, can be transmitted to the trainer/rehabilitation therapist and/or to the subject or to others, such as providers of the subject's health care. Specific programming can also be accessed and actively streamed to the user automatically, upon sensing an abnormal parameter value associated with a particular impairment or the need for training of a specific parameter desired. The subject with normal parameters desiring training can select specific programs to enhance eye fixation with activities to super-normal levels. The subject having an abnormal ocular parameter(s) can be trained with specific visual ocular tasks to rehabilitate the ocular parameter(s) which was abnormal. Eye movement and/or eye position and/or eye orientation changes, pupil size and eyeblinks can be measured with the VOV rehabilitation tasks or with the visual training tasks. The improvements can be determined by the measured data and wirelessly transmitted back to the cloud for data logging.

In another embodiment, the eye imaging module affixed or embedded in the FPE can assess the retina for anatomic changes, such as with vessels or the optic disc, biochemical changes, such as with protein or lipid biomarkers, or physiologic changes, such as blood flow or cerebrospinal fluid changes, as biomarkers to detect TBI.

In an embodiment, data obtained from the face protection equipment and methods described herein can be transmitted by wireless communication to a remote device.

In another embodiment, the raw data collected from the eye imaging sensor(s) and/or position sensor or eye imaging sensor(s) and/or position sensor and body movement sensor and/or position sensor is transmitted wirelessly, to an external source such as the cloud, or external device for further processing.

In an alternative embodiment, the face protection equipment can be connected wirelessly to a smart phone, iPad, or computer and push eye imaging or eye and head orientation responses to these devices.

Embodiments described herein can be used with a protective helmet including those designed for sport activities and/or industrial activities. Various embodiments can also be used for safety helmets, such as construction or industrial helmets, and helmets used by law enforcement, security and/or military forces.

Areas of Application

Sports. Embodiments of the invention(s) can be used in sport environments where ocular parameter measurement can help predict player performance, player fatigue, attention, cognition, and early detection of traumatic brain injury. Additionally, if an athlete had such an abnormality and could be given rehabilitation, this can correct the abnormality and allow the athlete to return to play activities sooner. Embodiments of the invention(s) can be used for TBI/concussion management, in which detection, quantification, and monitoring of concussions can be performed with the technology as well as determining when the athlete is safe to return to play, following a concussion, based on the eye movement responses. This technology can prevent the more serious recurrent concussions, especially if they are closely related to the previous concussion. Substance use impairment can also adversely affect ocular performance. Embodiments of the invention(s) can be used for impairment or performance screening and predict player performance based on eye fixation ability.

Medical. Embodiments of the present invention can be useful for centers that perform vestibular rehabilitation and athletic/vocational enhancement. Embodiments can be used specifically for cognitive impairment monitoring, mental health monitoring, behavioral health monitoring, neurologic health monitoring, monitoring eye disease, biochemical impairment monitoring, and physiologic impairment monitoring. Health monitoring with artificial intelligence (AI) with the technology discussed herein can collect, analyze, and interpret health-related data in real-time. AI algorithms or quantum algorithms can analyze historical health data to predict the likelihood of future health events. Early detection of health issues can allow for timely intervention and preventive measures.

This invention can provide objective tools for early detection of health-related biomarkers for neurologic impairments, including traumatic brain injury (TBI), biochemical impairments or physiologic impairments which would affect the human health condition.

Although the invention herein has been described with reference to embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

Further variations and modifications of the disclosed embodiments can also be used. The principles described here can also be used for applications other than sports. While the principles of the disclosure have been described above in connection with specific apparatuses and methods, it is understood that this description is made only by way of example and not as limitation on the scope of the disclosure.

What is claimed is:

1. A system for assessing a human health condition, wherein:
   the system comprises wearable face protection equipment;
   the face protection equipment comprises an eye imaging module;
   the eye imaging module is configured for imaging an eye component wherein the eye component is selected from the group of:
   a retina;
   a sclera;
   a cornea;
   an iris;
   a limbus;
   a pupil; and
   an eyelid;
   the eye imaging module determines eye information in response to imaging the eye component at a plurality of times, wherein the eye information is selected from the group of:
   eye orientation information at a plurality of times;
   pupil size at a plurality of times; and
   eyelid position information at a plurality of times;
   the system further comprises an electronic circuit;
   the electronic circuit is responsive to the eye information to generate an ocular parameter measurement selected from the group of:
   a saccade measurement;
   a vergence measurement;

a head static smooth pursuit measurement;
a head dynamic smooth pursuit measurement;
a gaze measurement;
an eye fixation measurement;
a pupil size change measurement; and
an eyeblink measurement;
the system is configured to assess a human health condition in response to the ocular parameter measurement from the electronic circuit; and
the assessed human health condition is selected from the group of:
normal human health:
a neurologic condition;
a mental health condition;
a behavioral health condition;
a biochemical health impairment; and
a physiologic impairment.

2. The system of claim 1, wherein:
the assessed human health condition comprises a neurologic condition; and
the neurologic condition comprises a traumatic brain injury.

3. The system of claim 2, wherein:
the eye imaging module comprises a first module for imaging a left eye and a second module for imaging a right eye; and
the first module and the second module each comprise an infrared light source, a prism or mirror, and a photodetector.

4. The system of claim 3, wherein:
the system further comprises a display;
the display is configured to present a training protocol to a user;
the eye imaging module is configured to measure and record eye information that is responsive to the user's response to the training protocol; and
the training protocol is responsive to the recorded eye information.

5. The system of claim 1, wherein:
the assessed human health condition comprises a mental health condition;
the mental health condition comprises a cognitive impairment;
the system is further configured to diagnose the cognitive impairment in response to health-related biomarkers that are detected in response to:
a detected abnormal ocular parameter;
and additional input selected from the group of:
health history; and
internal body medical imaging;
the abnormal ocular parameter is detected in response to:
the ocular parameter measurement from the electronic circuit; and
baseline values of ocular parameter measurements.

6. The system of claim 1 wherein:
the assessed human health condition comprises a condition selected from the group of:
a neurologic condition;
a biochemical impairment; and
a physiologic impairment; and
the system is configured for performing a pharmacologic intervention in response to the assessed human health condition.

7. The system of claim 6 wherein:
the assessed human health condition comprises a neurologic condition; and
the neurologic condition comprises a neurocognitive impairment selected from the group of:
Alzheimer's disease;
Parkinson's disease;
Lewy body dementia;
a frontotemporal impairment; and
a neuroviral impairment.

8. The system of claim 1, wherein:
the eye component comprises an eyelid;
the eye information comprises eyelid position at a plurality of times;
the ocular parameter measurement comprises eyeblinks;
the assessed human health condition comprises a physiologic impairment;
the physiologic impairment comprises fatigue; and
the physiologic impairment information is used as input for control of a vehicle.

9. The system of claim 1, wherein:
the assessed human health condition comprises a biochemical impairment;
the biochemical impairment comprises a metabolic dysfunction; and
the metabolic dysfunction comprises a hormonal abnormality.

10. The system of claim 1, wherein:
the face protection equipment further comprises a forward-facing camera;
the forward-facing camera is configured for measuring and recording light levels;
the eye component comprises a pupil;
the eye information comprises pupil size at a plurality of times; and
the ocular parameter measurement comprises a pupil size change measurement at a plurality of times;
the assessed human health condition comprises a behavioral health condition; and
the behavioral health condition comprises substance use impairment.

11. The system of claim 1, wherein:
the face protection equipment further comprises a forward-facing camera;
the forward-facing camera is configured for determining the location of a visual target in a scene;
the system is configured to measure eye fixation in response to:
the eye information; and
the visual target location information from the forward-facing camera.

12. The system of claim 1, wherein:
the ocular parameter measurement comprises a saccade measurement; and
the assessed human health condition comprises a neurologic condition; and
the neurologic condition comprises a cerebrovascular impairment selected from the group of:
a migraine;
a stroke;
a transient ischemic attack;
vascular dementia;
cerebrovascular stenosis; and
a cerebrovascular aneurysm.

13. The system of claim 1, wherein:
the system is further configured to diagnose the human health condition in response to health-related biomarkers that are detected in response to:

a detected abnormal ocular parameter;
an additional input selected from the group of:
  health history; and
  physical examination information; and
the abnormal ocular parameter is detected in response to:
  the ocular parameter measurement from the electronic circuit; and
  baseline values of ocular parameter measurements.

14. The system of claim 1, wherein:
the assessed human health condition comprises a behavioral health condition; and
the behavioral health condition comprises impairment from substance use.

15. The system of claim 1, wherein:
the assessed human health condition comprises a physiologic impairment;
the physiologic impairment comprises fatigue.

16. Face protection equipment configured for assessing human health, wherein:
the face protection equipment comprises an eye imaging module;
the eye imaging module is configured for imaging a retina, a sclera, a cornea, an iris, a limbus, a pupil, or an eyelid;
the eye imaging module is configured for imaging a human eye component at a plurality of times to determine eye information selected from the group of:
  eye orientation at a plurality of times;
  pupil size at a plurality of times; and
  eyelid position at a plurality of times;
the eye imaging module is further configured for transmitting the eye information to an electronic circuit that is configured for generating an ocular parameter measurement selected from the group of:
  a saccade measurement;
  a vergence measurement;
  a head static smooth pursuit measurement;
  a head dynamic smooth pursuit measurement;
  a gaze measurement;
  an eye fixation measurement;
  a pupil size change measurement; and
  an eyeblink measurement; and
the electronic circuit is further configured to assess a human health condition selected from the group of:
  normal human health:
  a neurologic condition;
  a mental health condition;
  a behavioral health condition;
  a biochemical health impairment; and
  a physiologic impairment.

17. The face protection equipment of claim 16, wherein:
the face protection equipment comprises wearable face protection equipment.

18. The face protection equipment of claim 16, wherein:
the human health condition comprises a physiologic impairment; and
the physiologic impairment comprises fatigue.

19. A method for assessing a human health condition, wherein:
the method comprises establishing an eye imaging module on face protection equipment;
using the eye imaging module to image a retina, a sclera, a cornea, an iris, a limbus, a pupil, or an eyelid at a plurality of times to determine eye information selected from the group of:
  eye orientation at a plurality of times;
  pupil size at a plurality of times; and
  eyelid position at a plurality of times; and
transmitting the eye information to an electronic circuit;
using the electronic circuit to generate an ocular parameter measurement selected from the group of:
  a saccade measurement;
  a vergence measurement;
  a head static smooth pursuit measurement;
  a head dynamic smooth pursuit measurement;
  a gaze measurement;
  an eye fixation measurement;
  a pupil size change measurement; and
  an eyeblink measurement; and
assessing the human health condition in response to the ocular parameter measurement, wherein the human health condition is selected from the group of:
  normal human health:
  a neurologic condition;
  a mental health condition;
  a behavioral health condition;
  a biochemical health impairment; and
  a physiologic impairment.

20. The method for assessing the human health condition of claim 19, wherein:
the human health condition comprises a biochemical health impairment; and
the biochemical health impairment is substance use impairment.

* * * * *